(12) United States Patent
Crawford et al.

(10) Patent No.: US 11,694,355 B2
(45) Date of Patent: *Jul. 4, 2023

(54) PREDICTIVE VISUALIZATION OF MEDICAL IMAGING SCANNER COMPONENT MOVEMENT

(71) Applicant: GLOBUS MEDICAL, INC., Audubon, PA (US)

(72) Inventors: Neil Crawford, Chandler, AZ (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 33 days.

This patent is subject to a terminal disclaimer.

(21) Appl. No.: 17/382,556

(22) Filed: Jul. 22, 2021

(65) Prior Publication Data
US 2021/0350567 A1    Nov. 11, 2021

Related U.S. Application Data

(63) Continuation of application No. 16/742,994, filed on Jan. 15, 2020, now Pat. No. 11,100,668, which is a continuation of application No. 15/948,348, filed on Apr. 9, 2018, now Pat. No. 10,573,023.

(51) Int. Cl.
| | |
|---|---|
| *G06T 7/70* | (2017.01) |
| *G06T 19/00* | (2011.01) |
| *A61B 6/00* | (2006.01) |
| *G06T 7/20* | (2017.01) |
| *G06F 3/01* | (2006.01) |

(52) U.S. Cl.
CPC ............. *G06T 7/70* (2017.01); *A61B 6/4405* (2013.01); *A61B 6/4441* (2013.01); *A61B 6/547* (2013.01); *G06F 3/011* (2013.01); *G06T 7/20* (2013.01); *G06T 2207/20221* (2013.01); *G06T 2207/30241* (2013.01); *G06T 2207/30244* (2013.01)

(58) Field of Classification Search
CPC ............................. G06T 7/70; G06T 19/006
See application file for complete search history.

(56) References Cited

U.S. PATENT DOCUMENTS

| | | | |
|---|---|---|---|
| 1,068,626 | A | 7/1913 | Buck |
| 4,150,293 | A | 4/1979 | Franke |
| 4,737,038 | A | 4/1988 | Dostoomian |
| 4,757,710 | A | 7/1988 | Haynes |
| 5,246,010 | A | 9/1993 | Gazzara et al. |
| 5,354,314 | A | 10/1994 | Hardy et al. |

(Continued)

OTHER PUBLICATIONS

US 8,231,638 B2, 07/2012, Swarup et al. (withdrawn)

*Primary Examiner* — Yi Yang

(57) ABSTRACT

An augmented reality system is provided for use with a medical imaging scanner. The AR system obtains a digital image from a camera, and identifies a pose of a gantry of the medical imaging scanner based on content of the digital image. The gantry includes a movable C-arm supporting an imaging signal transmitter and a detector panel that are movable along an arc relative to a station. A range of motion of the movable C-arm along the arc is determined based on the pose. A graphical object is generated based on the range of motion and the pose, and is provided to a display device for display as an overlay relative to the medical imaging scanner.

19 Claims, 16 Drawing Sheets

(56) References Cited

U.S. PATENT DOCUMENTS

| | | |
|---|---|---|
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |

(56) References Cited

U.S. PATENT DOCUMENTS

| | | |
|---|---|---|
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |

(56) References Cited

U.S. PATENT DOCUMENTS

| | | |
|---|---|---|
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,005,113 B2 | 4/2015 | Scott et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,271,633 B2 | 3/2016 | Scott et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,565,997 B2 | 2/2017 | Scott et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 9,962,069 B2 | 5/2018 | Scott et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0159220 A1* | 7/2006 | Heuscher ............ A61B 6/482 378/9 |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |

(56) References Cited

U.S. PATENT DOCUMENTS

| | | |
|---|---|---|
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1* | 6/2008 | Allred .................. A61B 5/062 382/131 |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0224904 A1* | 9/2011 | Feiten .................. A61B 6/4441 378/205 |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1* | 12/2013 | Isaacs .................. G16H 30/20 345/634 |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1* | 2/2014 | Siewerdsen ........... A61B 34/20 348/77 |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |

(56) References Cited

U.S. PATENT DOCUMENTS

| | | |
|---|---|---|
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0324580 A1* | 11/2016 | Esterberg ............... A61B 34/10 |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0228351 A1 | 8/2018 | Scott et al. |
| 2018/0373412 A1* | 12/2018 | Reif .................... G06F 3/04815 |
| 2019/0371012 A1* | 12/2019 | Flexman ............. G09B 19/003 |

* cited by examiner

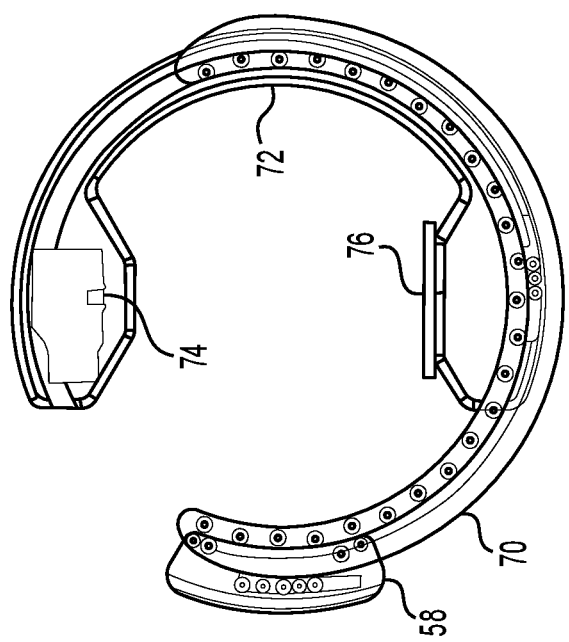

PREDICTIVE VISUALIZATION OF MEDICAL IMAGING SCANNER COMPONENT MOVEMENT

CROSS-REFERENCE TO RELATED APPLICATIONS

The present application is a continuation of U.S. patent application Ser. No. 16/742,994, filed Jan. 15, 2020, which is a continuation of U.S. patent application Ser. No. 15/948,348, filed Apr. 9, 2018, all of which are incorporated herein by reference in their entity.

TECHNICAL FIELD

The present disclosure relates to medical imaging scanner systems, and more particularly, controlled placement and movement of components of medical imaging scanner systems.

BACKGROUND OF THE DISCLOSURE

Healthcare practices have shown the tremendous value of three-dimensional (3-D) medical imaging scanner systems such as computed tomography (CT) imaging, as a diagnostic tool in the Radiology Department. These systems generally contain a fixed bore into which the patient enters from the head or foot. Other areas of care, including the operating room, intensive care departments and emergency departments, rely on two-dimensional imaging (fluoroscopy, ultrasound, 2-D mobile X-ray) as the primary means of diagnosis and therapeutic guidance.

Mobile medical imaging scanner systems have evolved for non-radiology department use and provide patient-centric 3-D imaging. Small scale mobile systems have evolved for use in the operating room, procedure rooms, intensive care units, emergency departments and other parts of the hospital, in ambulatory surgery centers, physician offices, and the military battlefield, and which can image patients in any direction or height and produce high-quality 3-D images. These systems include intra-operative CT and magnetic resonance imaging (MRI) scanners, and related robotic systems that aid in their use or movement. The systems can include 180-degree movement capability (via movable "C-arms" for imaging). The systems may be particularly useful during surgery or other medical procedures when a real-time image is desired to guide personnel through a medical procedure.

Medical imaging scanner systems require a high level of operator skill and can require calibration operations to properly position the movable imaging components for a patient scan, and which can be complicated when a patient is immobilized on a bed. In an operating room or operating theatre, the size and weight of the system and the presence of numerous required personnel and other medical equipment can make it difficult to precisely position the movable imaging components for a scan of a patient without leading to collision of the movable imaging components with the patient, personnel, and/or other medical equipment.

SUMMARY OF THE DISCLOSURE

Various embodiments of the present disclosure provide an improved user interface for operating a medical imaging scanner system.

Some embodiments of the present disclosure are directed to an augmented reality (AR) system for use with a medical imaging scanner. The system includes a processor and a memory which stores program code that is executable by the processor to perform operations. The operations include obtaining a digital image from a camera, and identifying a pose of a gantry of the medical imaging scanner based on content of the digital image. The gantry includes a movable C-arm supporting an imaging signal transmitter and a detector panel that are movable along an arc relative to a station. The operations determine a range of motion of the movable C-arm along the arc based on the pose. The operations further generate a graphical object based on the range of motion and the pose, and provide the graphical object to a display device for display as an overlay relative to the medical imaging scanner.

Various further embodiments are directed to displaying an arcuate object as an overlay relative to the gantry and with a pose that indicates a range of motion of at least one of the imaging signal transmitter and the detector panel. A circular object may be displayed with a pose that indicates an interior region of the movable C-arm that will not be contacted by the at least one of the imaging signal transmitter and the detector panel when moved along the arc through the range of motion. The system may perform a collision alert action responsive to determining that a physical object which is separate from the gantry has a surface that extends from a location within the circular object displayed on the display device to another location that is outside the circular object. The collision alert action may include providing another graphical object for display as an overlay relative to the physical object and that identifies the physical object as being a collision risk, and/or may include communicating a command to the medical imaging scanner that disables electronic movement of the movable C-arm at least in a direction that may collide with the physical object. The system may generate an animation of the motion of the gantry through its range of motion. The system may display virtual imaging signal beams that extend between the present locations of the X-ray beam and the detector panel and/or that extend between earlier defined locations of the X-ray beam and the detector panel. These and additional embodiments are described in further detail below.

Still other related embodiments are directed to another AR system for use with a medical imaging scanner. The AR system may include a stand-alone headset or a headset that is communicatively connected to an AR predictive visualization computer. The AR system includes a camera, a display device with a see-through display screen that displays graphical images while allowing transmission of incident ambient light therethrough, and at least one processor that performs operations. The operations include obtaining a digital image from the camera, and identifying a pose of a gantry of the medical imaging scanner based on content of the digital image. The gantry includes a movable C-arm supporting an imaging signal transmitter and a detector panel that are movable along an arc relative to a station. The operations further include determining a range of motion of the movable C-arm along the arc based on the pose. The operations generate a graphical object based on the range of motion and the pose, and providing the graphical object to the display screen for display as an overlay relative to the medical imaging scanner.

When the AR system is a stand-alone headset, the camera, the display device, and the at least one processor are each supported by a headset frame.

When the AR system uses an AR headset that is communicatively connected to an AR predictive visualization computer, the AR headset includes a network interface, the camera, the display device, and a first processor which is configured to perform the operation of obtaining the digital image from the camera and an operation of communicating the digital image through the network interface toward the AR predictive visualization computer. The AR predictive visualization computer includes a network interface configured to communicate with the network interface of the AR headset, a second processor which is configured to perform the operations of identifying the pose of the gantry, determining the range of motion of the movable C-arm, generating the graphical object, and providing the graphical object through the network interface toward the AR headset for display on the display screen.

It is noted that aspects described with respect to one embodiment disclosed herein may be incorporated in different embodiments although not specifically described relative thereto. That is, all embodiments and/or features of any embodiments can be combined in any way and/or combination. Moreover, apparatus, systems, methods, and/or computer program products according to embodiments will be or become apparent to one with skill in the art upon review of the following drawings and detailed description. It is intended that all such additional apparatus, systems, methods, and/or computer program products be included within this description and protected by the accompanying claims.

BRIEF DESCRIPTION OF DRAWINGS

Other features of embodiments will be more readily understood from the following detailed description of specific embodiments thereof when read in conjunction with the accompanying drawings, in which:

FIGS. 9A-9G illustrate the 360 degree rotation of the gantry in 60 degree increments.

DETAILED DESCRIPTION

Figure 1:
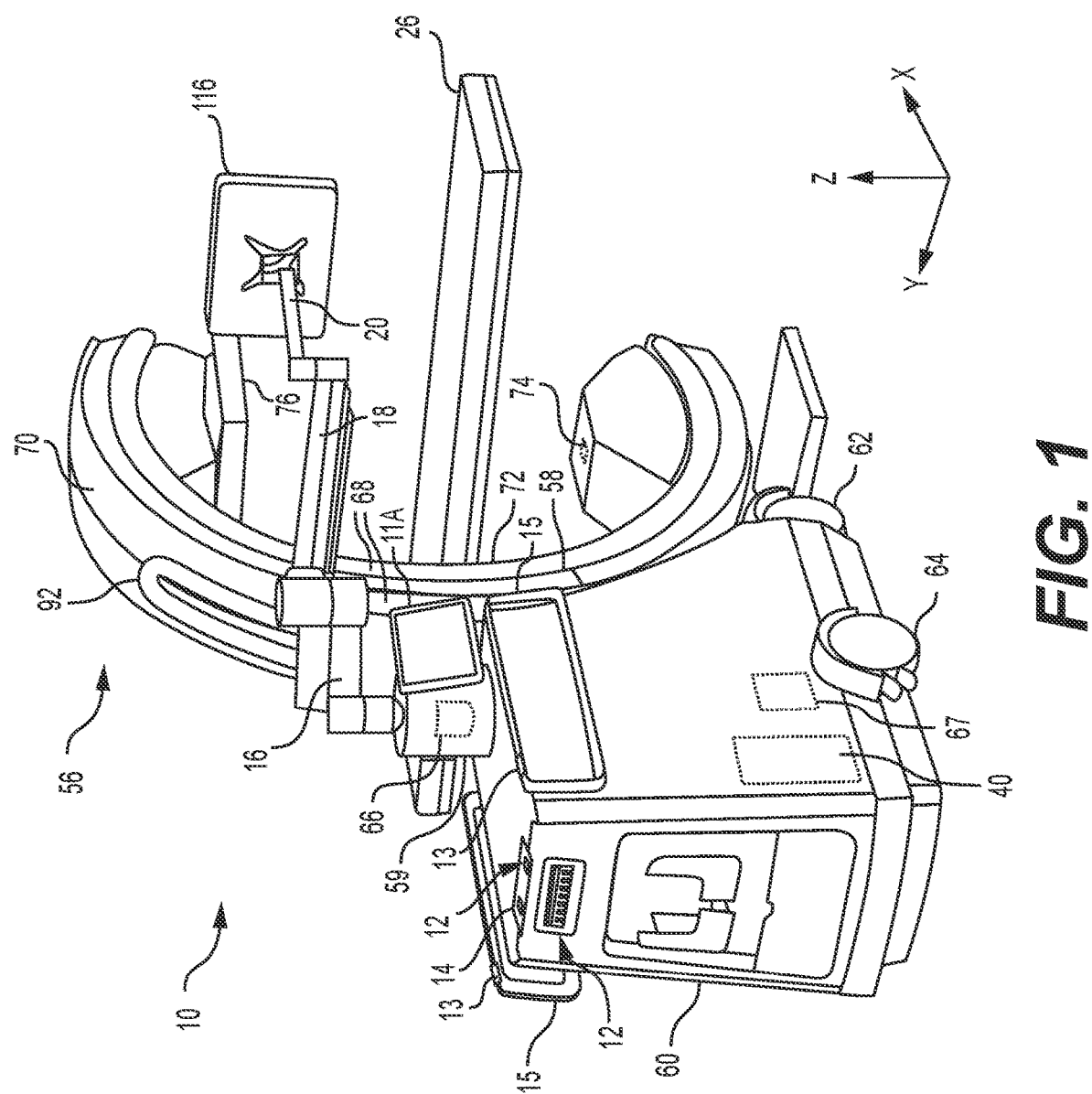
FIG. 1 is a perspective rear view of an imaging system according to some embodiments of the present disclosure.

In the following detailed description, numerous specific details are set forth in order to provide a thorough understanding of embodiments of the present disclosure. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

When working with medical imaging scanner systems, it may not be safe for users to assume that the pathway of components that move during medical imaging is clear, since they may collide with a patient or other equipment. One approach for avoiding such collisions, is to visually estimate whether components of the scanner system will be clear of collisions along their range of motion and, if not, to then stop a scan, adjust positioning of the scanner system and/or object in the pathway, and re-start imaging. Another approach is to perform a dry run in which the scanner system moves through its entire pathway while observing for possible collisions, and while the imaging signal transmitter is unpowered. These approaches undesirably consume time, personnel resources, and electrical power, and may lead to unnecessary exposure to imaging signals, such as x-rays, for personnel and patients.

Various embodiments of the present disclosure are directed to an improved user interface for operating a medical imaging system having movable scanner components. An augmented reality (AR) system enables a user who is wearing an AR headset or looking at a video monitor of the operating room scene to visually observe graphical objects that are displayed as an overlay on the imaging system to illustrate the range of motion of the movable scanner components. The graphical objects may provide predictive visualization to the user of how the scanner components can move during an imaging scan. The AR system may display a graphical object that indicates to the user the location of a space, defined by motion of the scanner components, in which a surgical table or other object can be positioned while avoiding possible collision with the movable scanner components during an imaging scan. The AR system may display a graphical object that highlights a physical object that is in a collision pathway of the movable components. The AR system may display virtual imaging signal beams that extend between a pair of an imaging signal transmitter and a detector panel which are located at present locations, defined previous locations, and/or defined future locations, to facilitate the user's positioning of these components relative to a patient. As used herein, a "user" may be, but is not limited to, a physician, nurse, or other medical professional.

As will be explained in further detail below, an AR system obtains a digital image from a camera, such as from a camera mounted on an AR headset or on a tripod, and identifies a pose of a gantry of a medical imaging scanner based on content of the digital image. As used herein, the term pose refers to the dimensional location and/or angular orientation of an object. The gantry includes a movable C-arm supporting an imaging signal transmitter and a detector panel that are movable along an arc relative to a station. A range of motion of the movable C-arm along the arc is determined based on the pose. A graphical object is generated based on the range of motion and the pose, and is provided to a display device, such as to a display screen of an AR headset or to a graphics layer superimposed on a video stream layer on a computer monitor, for display as an overlay on the view of the portable medical imaging scanner.

Various further embodiments are directed to displaying an arcuate object as an overlay relative to the gantry and with a pose that indicates a range of motion of at least one of the imaging signal transmitter and the detector panel. A circular object may be displayed with a pose that indicates an interior region of the movable C-arm that will not be contacted by the imaging signal transmitter and/or the detector panel when moved along the arc through the range of motion. The system may perform a collision alert action responsive to determining that a physical object, which is separate from the gantry, has a surface that extends from a location within the circular object displayed on the display device to another location that is outside the circular object. The collision alert action may include displaying another graphical object overlaid relative to the physical object and that identifies the physical object as being a collision risk, and/or may include communicating a command to the portable medical imaging scanner that disables electronic movement of the movable C-arm at least in a direction that may collide with the physical object. The system may generate an animation of the motion of the gantry through its range of motion. The system may display virtual imaging signal beams that extend between the present locations of the X-ray beam and the detector panel and/or that extend between earlier defined locations of the X-ray beam and the detector panel. These and additional embodiments are described in further detail below.

In the following description, the components and operation of an example medical imaging scanner system are described with reference to FIGS. 1 through 9G. An AR system is then described with reference to FIGS. 10 through 16 and which may be used with the medical imaging scanner shown in FIGS. 1 through 9G.

Example Medical Imaging Scanner System

FIG. 1 is a schematic diagram showing a medical imaging scanner system 10 (also "scanner system"), such as a computerized tomographic (CT) x-ray scanner, in accordance with one embodiment of the disclosure. The imaging system 10 includes a movable station 60 and a gantry 56. The movable station includes a vertical shaft 59 and a gantry mount 58 which is rotatably attached to the vertical shaft. The movable station 60 includes two front omni-directional wheels 62 and two rear omni-directional wheels 64, which together provide movement of the movable station 60 in any direction in an X-Y plane. The horizontal X-Y plane is depicted in the Cartesian coordinate system X, Y axes shown in FIG. 1, along with a vertical axis Z. The omni-directional wheels 62, 64 can be obtained, for example, from Active Robots Limited of Somerset, U.K. A pair of handles 13 mounted to the housing of the movable station 60 allow a user to manually maneuver the station.

A motor 66 attached to the vertical shaft 59 is designed to rotate the gantry mount 58 full 360 degrees about the X-axis and a motor 67 moves the gantry mount 58 vertically along the z-axis under the control of the motion control module 51.

The gantry 56 includes a first C-arm 70 slidably coupled to the gantry mount 58 and a second C-arm 72 which is slidably coupled to the first C-arm. In the embodiment shown, the first and second C-arms 70, 72 are outer and inner C-arms, respectively. In the embodiment shown, the outer and inner C-arms 70, 72 are partially-circular in shape and rotate circumferentially about a central axis so as to allow imaging of a patient who is lying in bed 26 without the need to transfer the patient.

An imaging signal transmitter 74 such as an X-ray beam transmitter is mounted to one side of the second C-arm 72 while a detector panel 76 such as an X-ray detector array is mounted to the other side of the second C-arm and faces the transmitter 74. In one embodiment, the imaging signal transmitter 74 transmits an X-ray beam for receipt by an X-ray detector component of the detector panel 76 after passing through a relevant portion of a patient (not shown) who is supported by the table 26.

In one embodiment, the system 10 is a multi-modality x-ray imaging system which can be used during surgery. Imaging modalities may include, but are not limited to, fluoroscopy, 2D Radiography, and Cone-beam CT. Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (cone beam 3D imaging or cone beam computer tomography) also referred to as C-arm CT, is a medical imaging technique consisting of X-ray computed tomography where the X-rays are divergent, forming a cone. Magnetic resonance imaging (MRI) may also be employed, with suitable precautions for using powerful magnets and controlling the magnetic fields they generate.

The movable station 60 includes an imaging controller system 40 which may serve a dual operational function of (1) controlling the movement of the omni-directional wheels 62, 64, gantry mount 58 and the gantry 56 to position the imaging signal transmitter 74 in relation to the patient, and other component movements as needed, and (2) controlling imaging functions for imaging the patient once proper positioning has been achieved.

Figure 2:
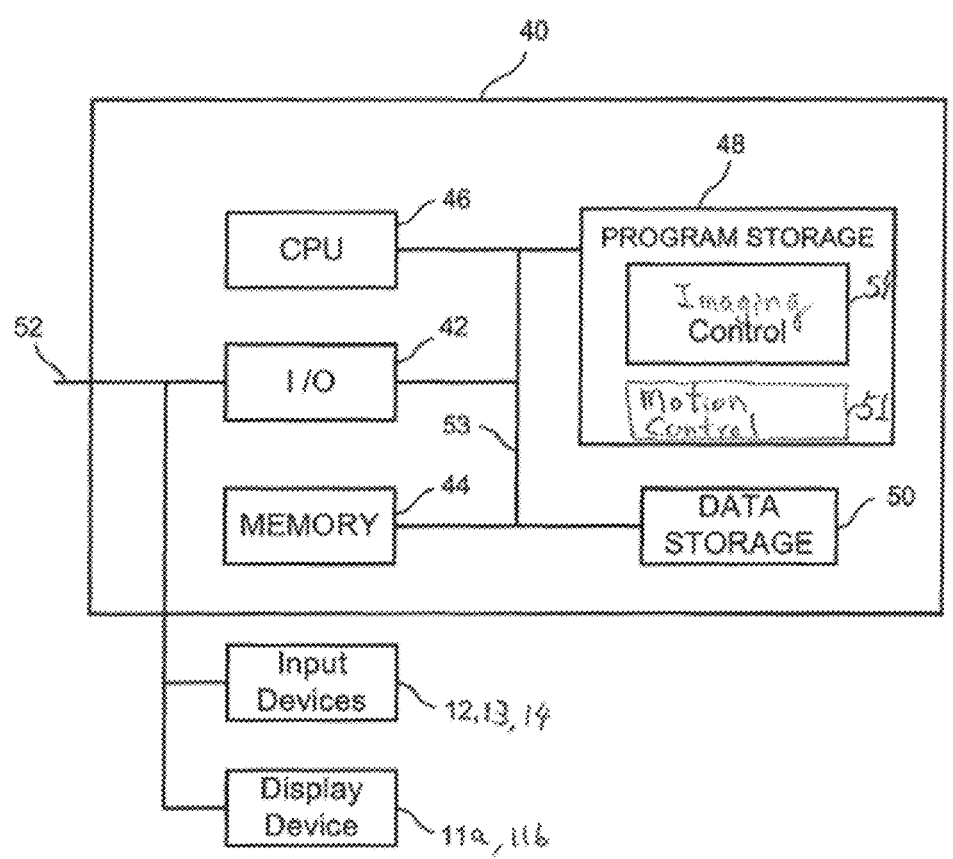
FIG. 2 is a schematic diagram of an imaging controller system 40 according to some embodiments of the present disclosure.
Figure 4:
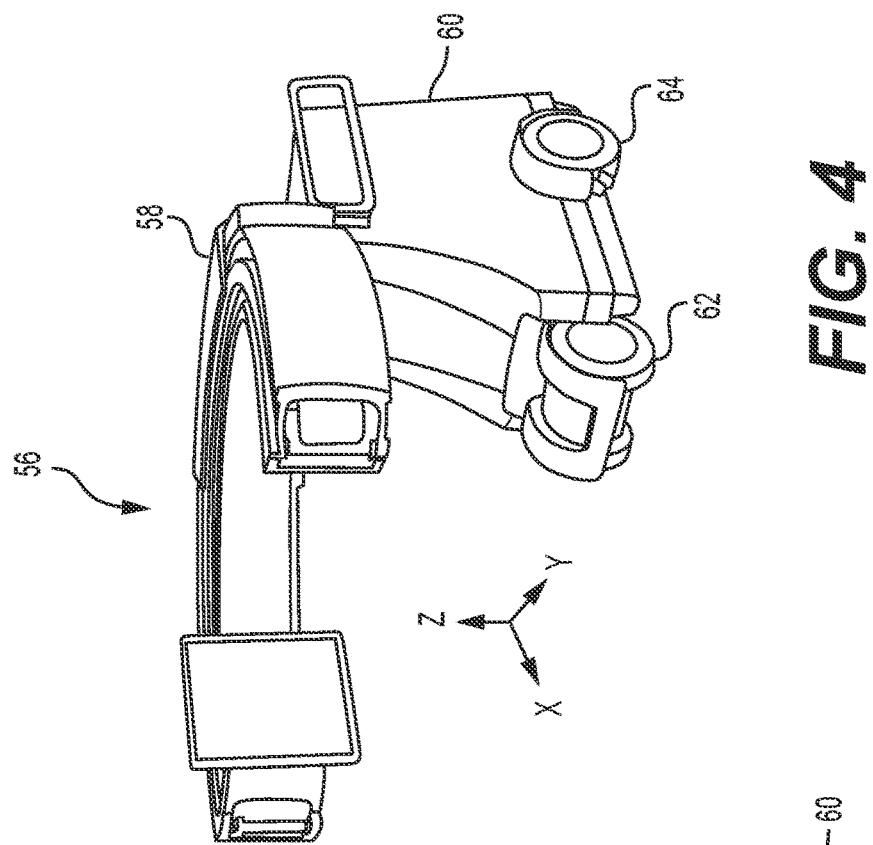
FIG. 4 is a perspective view of the imaging system of FIG. 1 in which the gantry has been rotated about the X-axis by 90 degrees.

Referring now to FIG. 2, the imaging controller system 40 is connected to a communication link 52 through a network I/O interface 42 such as a USB (universal serial bus) interface, which receives information from and sends information over the communication link 52. The imaging controller system 40 includes memory storage 44 such as RAM (random access memory), processor (CPU) 46, program storage 48 such as ROM or EEPROM, and data storage 50 such as a hard disk, all commonly connected to each other through a bus 53. The program storage 48 stores, among others, imaging control module 54 and motion control module 51, each containing software to be executed by the processor 46. The motion control module 51 executed by the processor 46 controls the wheels 62, 64 of the movable station 60 and various motors in the gantry mount 58 and gantry 56 to position the station 60 near the patient and position the gantry in an appropriate position for imaging a relevant part of the patient. The motion control module may also control additional components used for positioning, as explained below.

The imaging control module 54 executed by the processor 46 controls the imaging signal transmitter 74 and detector panel 76 to image the patient body. In one embodiment, the imaging control module images different planar layers of the body and stores them in the memory 44. In addition, the imaging control module 54 can process the stack of images stored in the memory 44 and generate a three dimensional image. Alternatively, the stored images can be transmitted through the network I/O interface 42 to a host system (not shown) for image processing.

The motion control module 51 and imaging control module 54 include a user interface module that interacts with the user through the display devices 11a and 11b and input devices such as keyboard and buttons 12 and joy stick 14. Strain gauges 13 mounted to the handles 15 are coupled to the I/O device 42 and conveniently provide movement of the movable station 12 in any direction (X, Y, Wag) while the user is holding the handles 15 by hand, as will be discussed in more detail below. The user interface module assists the user in positioning the gantry 56. Any of the software program modules in the program storage 48 and data from the data storage 50 can be transferred to the memory 44 as needed and is executed by the CPU 46. The display device 11a is attached to the housing of the movable station 60 near the gantry mount 58 and display device 11b is coupled to the movable station through three rotatable display arms 16, 18 and 20. First display arm 16 is rotatably attached to the movable station 60, second display arm 18 is rotatably attached to the first arm 16 and third display arm 20 is rotatably attached to the second display arm. The display devices 11a, 11b can have touch screens to also serve as input devices through the use of user interface modules in the modules 51 and 54 to provide maximum flexibility for the user.

Navigation markers 68 may be connected to the gantry mount 58 and may be connected to the imaging controller system 40 through the link 52. Under the control of the motion control module 51, the markers 68 allow automatic or semi-automatic positioning of the gantry 56 in relation to the patient bed or (operating room) table via a navigation system (not shown). The markers 68 can be configured to have their pose optically tracked, electromagnetically tracked, radiofrequency tracked (e.g., triangulation based on time-of-arrival of defined signals at spaced-apart receivers or from spaced-apart transmitters), or the like. The markers may also be connected to other convenient and useful places, e.g., on the patient bed, or otherwise, so that the marker or markers will be visible in the images taken and may be used to orient connecting images when more than one image is taken of a patient, or other object to be imaged. The markers may also contribute to merging or coordinating multiple images when more than one image is taken.

Information can be provided by the navigation system to command the gantry 56 or system 10 to precise locations. In one example, a surgeon holds a navigated probe at a desired orientation for the imaging system 10 to acquire a fluoroscopic or radiographic image along that specified trajectory. Advantageously, this method of defining the trajectory of an x-ray shot will remove the need for scout shots thus reducing x-ray exposure to the patient and operating room (OR) staff. The navigation markers 68 on the gantry 56 will also allow for automatic registration of 2D or 3D images acquired by the system 10. The markers 68 will also allow for precise repositioning of the system 10 in the event the patient has moved. The markers may be radiopaque or made from other material that makes coordination or navigation easy for the imaging specialists or other medical professionals. The navigation probes or markers may be placed as desired, e.g., nearby or on the object to be imaged, so that the markers do not interfere with the imaging or its interpretation.

In the embodiment shown, the system 10 provides a large range of motion in the 6-degrees of freedom ("DOF") described below. Under the control of the motion control module 51, there are two main modes of motion: positioning of the movable station 60 and positioning of the gantry 56. Other positioning modes are described and may also be included.

The movable station 60 positioning is accomplished via the four omni-directional wheels 62, 64. These wheels 62, 64 allow the movable station 60 to be positioned in all three DOF about the horizontal plane (X, Y, Wag). "Wag" is a system 10 rotation about the vertical axis (Z-axis), "X" is a system forward and backward positioning along the X-axis, and "Y" is system 10 lateral motion along the Y-axis. Under the control of the control module 51, the system 10 can be positioned in any combination of X, Y, and Wag (Wag about any arbitrary Z-axis due to use of omni-directional wheels 62, 64) with unlimited range of motion. In particular, the omni-directional wheels 62, 64 allow for positioning in tight spaces, narrow corridors, or for precisely traversing up and down the length of an OR table or patient bed.

The gantry 56 positioning is accomplished about (Z, Tilt, Rotor). "Z" is gantry 56 vertical positioning, "Tilt" is rotation about the horizontal axis parallel to the X-axis as described above, and "Rotor" is rotation about the horizontal axis parallel to the Y-axis as described above.

Together with the movable station 60 positioning and gantry 56 positioning, the system 10 provides a range of motion in six DOF (X, Y, Wag, Z, Tilt and Rotor) to place the movable station 60 and the imaging signal transmitter 74 and detector panel 76 precisely where they are needed. Advantageously, 3-D imaging can be performed regardless of whether the patient is standing up, sitting up or lying in bed and without having to move the patient.

Precise positions of the system 10 can be stored in the storage memory 50 and recalled at any time by the motion control module 51. This is positional storage mechanism not limited to gantry 56 positioning but also includes system 10 positioning due to the omni-directional wheels 62, 64, and other axes of motion, as described below.

Figure 3:
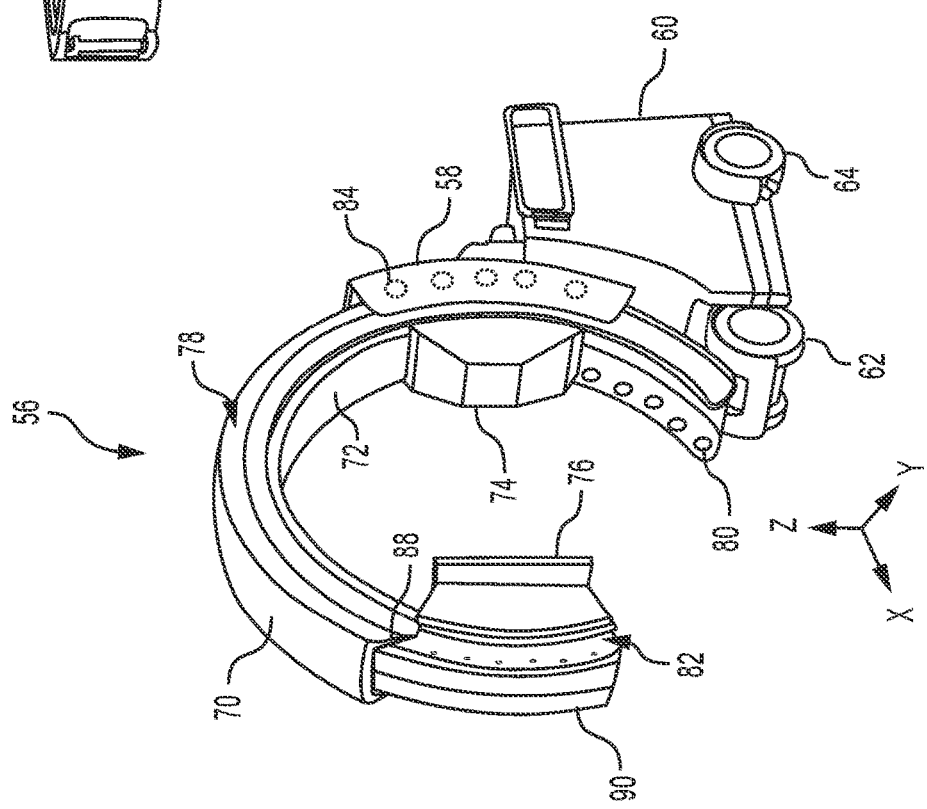
FIG. 3 is a perspective front view of the imaging system of FIG. 1.

As shown in FIG. 3, each of the gantry mount 58, outer C-arm 70 and inner C-arm 72 respectively has a pair of side frames 86, 88, 90 that face each other. A plurality of uniformly spaced rollers 84 are mounted on the inner sides of the side frames 86 of the gantry mount 58. The outer C-arm 70 has a pair of guide rails 78 on the outer sides of the side frames 88. The rollers 84 are coupled to the guide rails 78. As shown, the rollers 84 and the guide rails 78 are designed to allow the outer C-arm 70 to telescopically slide along the gantry mount 58 through its permitted range of motion so as to permit a range of motion of at least a 180 degree rotation of the C-arm about its central axis relative to the gantry mount.

A plurality of uniformly spaced rollers 80 are mounted on the inner sides of the side frames 88 of the outer C-arm 70. The inner C-arm 70 has a pair of guide rails 82 on the outer sides of the side frames 90. The rollers 80 are coupled to the guide rails 82. As shown, the rollers 80 and the guide rails 82 are designed to allow the inner C-arm 72 to telescopically slide along the outer C-arm 70 through its permitted range of motion so as to permit a range of motion of at least 180 degree rotation of the C-arm about its central axis relative to the outer C-arm.

Thus, the present disclosure as disclosed herein advantageously allows the gantry 56 to rotate about its central axis through its permitted range of motion, e.g., a full 360 degrees, to provide the maximum flexibility in positioning the imaging system 10 with minimum disturbance of the patient.

Figure 5:
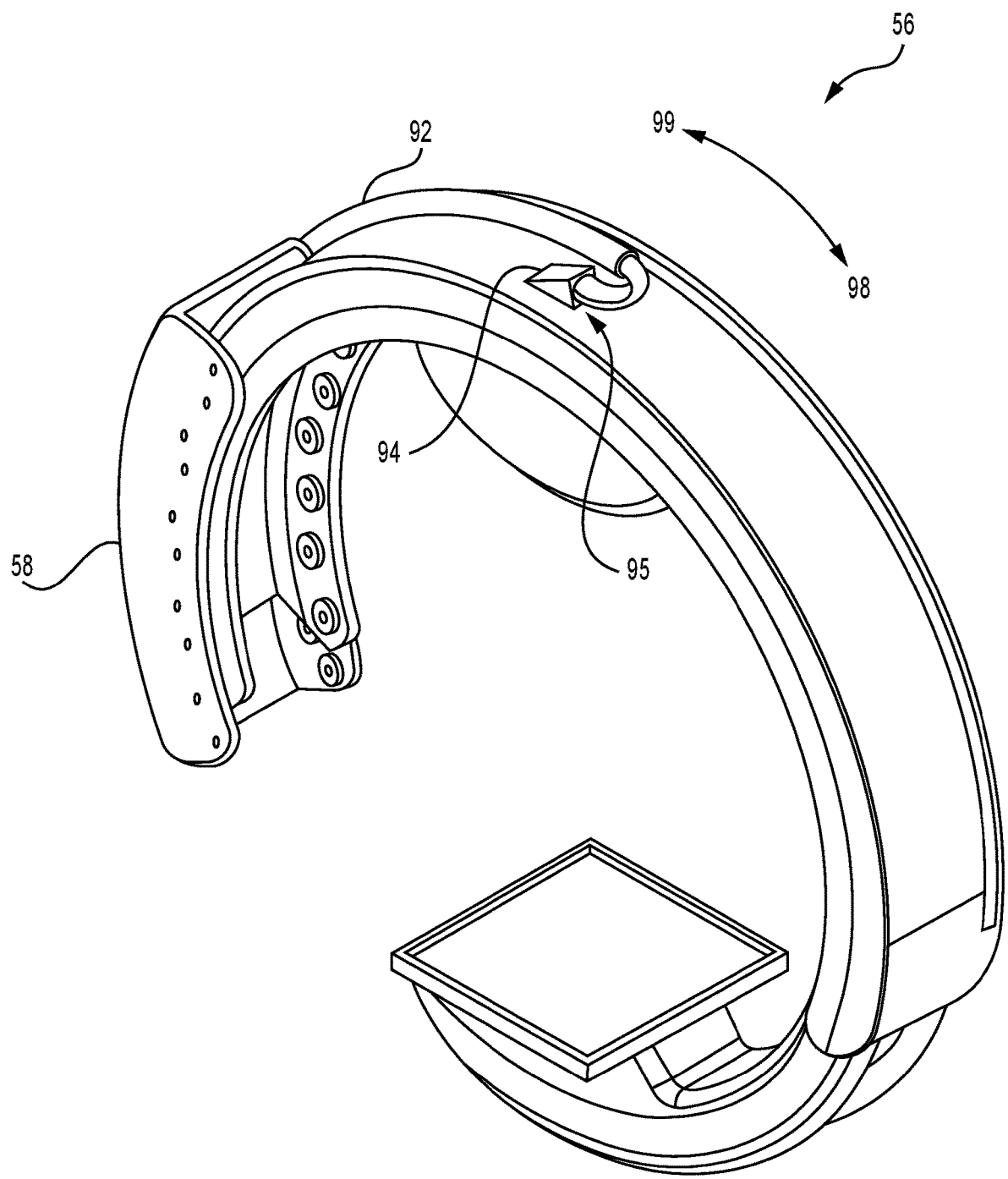
FIG. 5 is a perspective view of the gantry partially showing a cabling arrangement.
Figure 6:
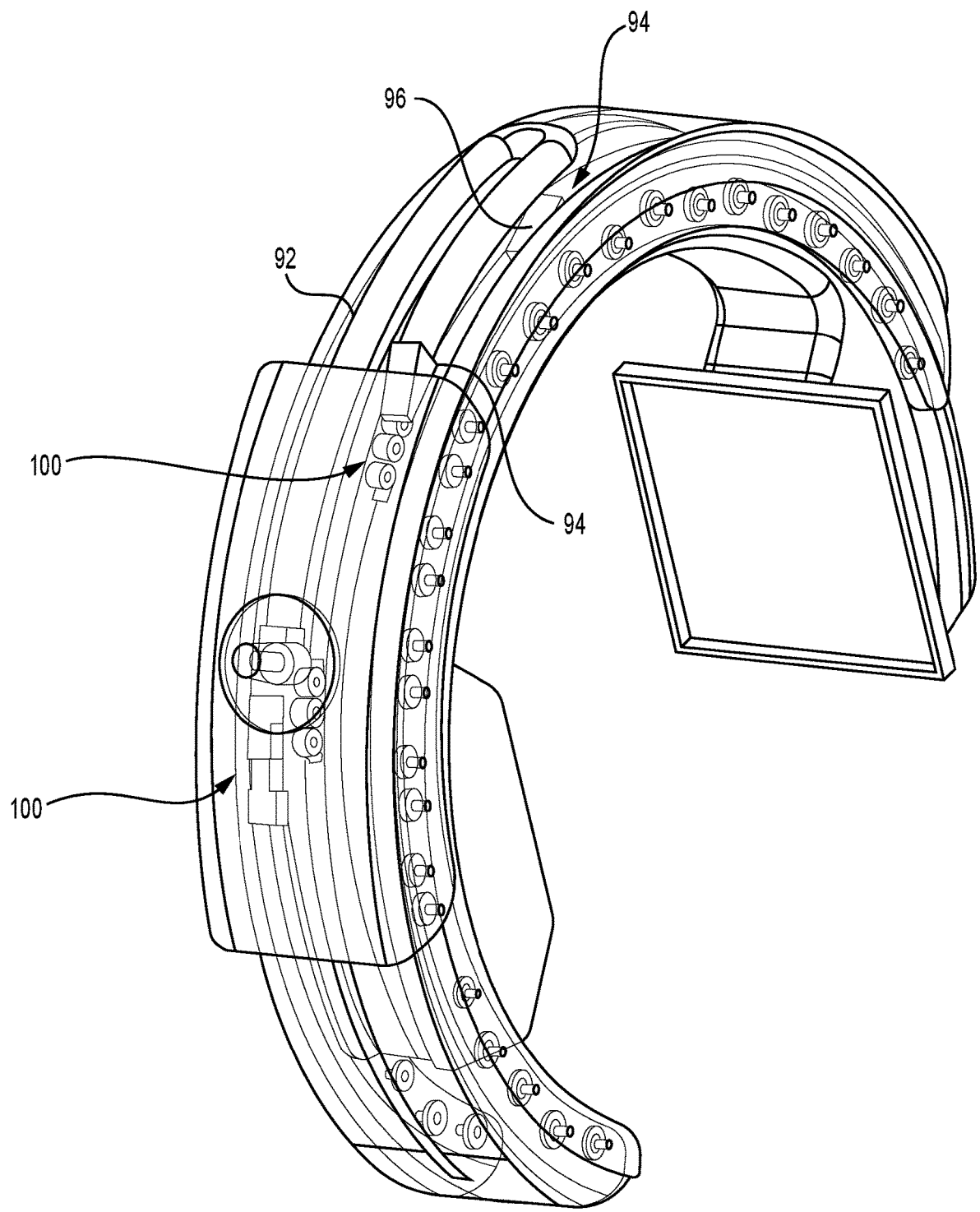
FIG. 6 is a perspective view of the gantry showing the cabling arrangement.
Figure 7:
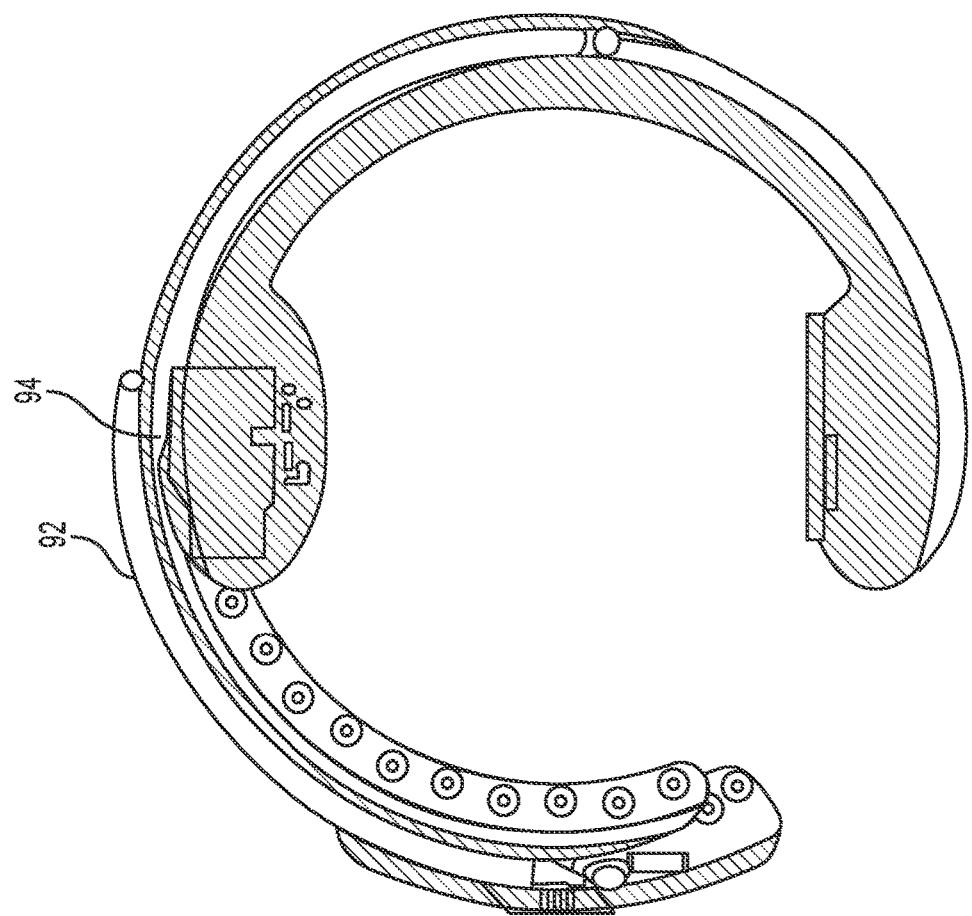
FIG. 7 is a side view of the gantry showing the cabling arrangement.

In another aspect of the present disclosure, a unique cabling arrangement is provided to make the imaging system 10 more compact and visually more appealing. As shown in FIGS. 5 and 6, a cable carrier/harness 92 contains electrical cables to carry signals between the imaging controller system 40 and various motors, X-ray transmitter 74, detector panel 76 and various electronic circuits in the gantry 56. A first cable router 94 is mounted to the outer surface of the outer C-arm 70 and a second cable router 96 is mounted to the outer surface of the inner C-arm 72. Each cable router 94, 96 has a through-hole 95, 97 through which the cable carrier 92 passes.

The cable carrier 92 extends from the gantry mount 56 over the outer surface of the first C-arm 70, through the through-hole 95 of the first cable router 94 and over an outer surface of the second C-arm 72. The cable carrier 92 overlying the first C-arm 70 extends in a first circumferential direction (clock-wise as shown) 98 and enters the first cable router 94 in a second circumferential direction (counter clock-wise as shown) 99 opposite to the first circumferential direction to create a 180 degree service loop over the outer surface of the first C-arm.

From there, the cable carrier 92 extends in the first circumferential direction 98 and enters the second cable router in the second circumferential direction 99 to create another service loop over the outer surface of the second C-arm 72.

The particular locations of the first and second cable routers 94, 96 combined with the service loops allow slack in the cable carrier 92 to provide the gantry 56 with full 360 degrees rotation without tangling or causing stress in the cable carrier. In the embodiment shown, the routers are mounted near the midpoint of the C-arms.

Figure 8:
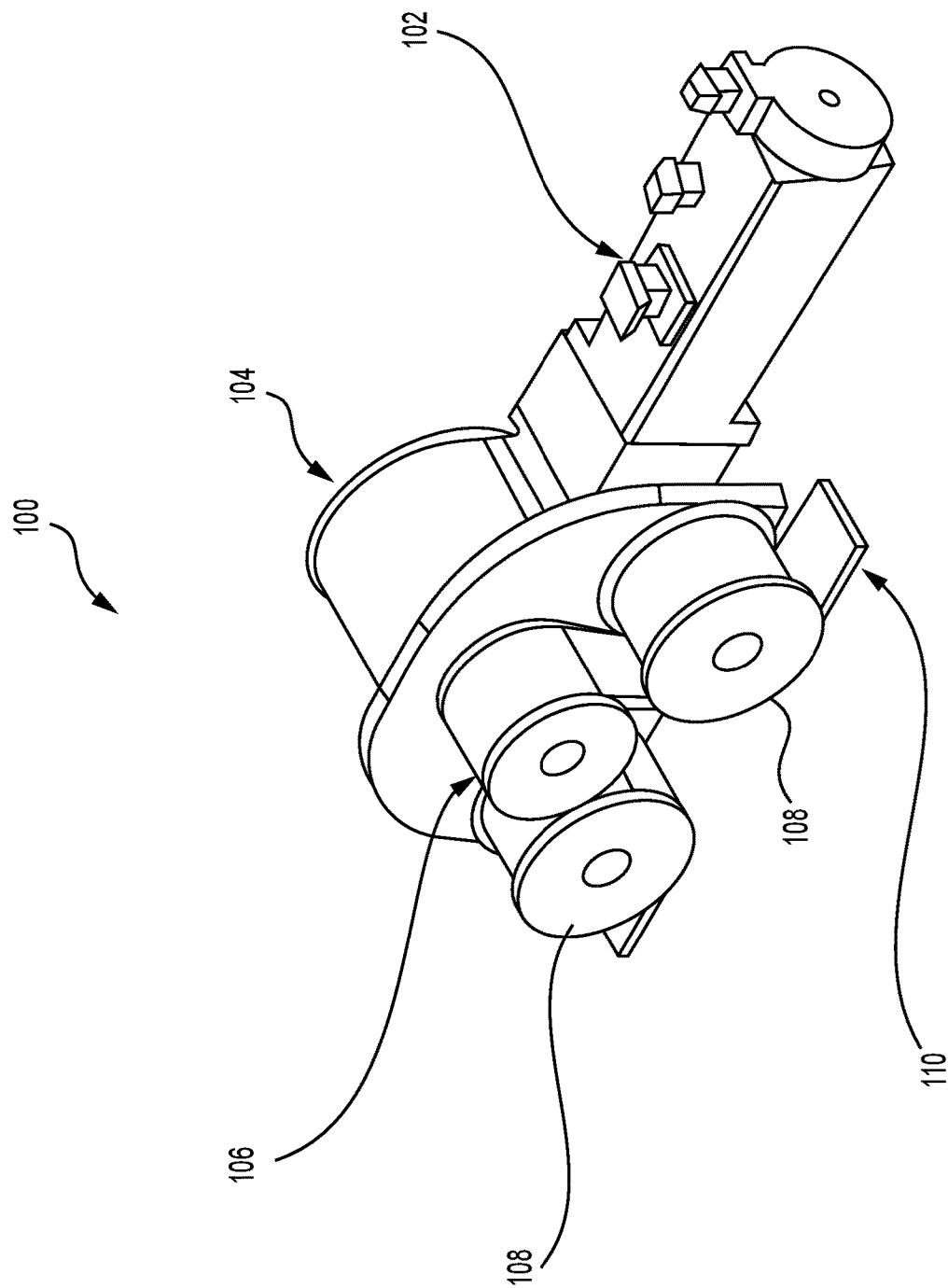
FIG. 8 illustrates a motor assembly for telescopically controlling the C-arms of the gantry.

FIG. 8 illustrates one embodiment of a motor assembly 100 that may be used for telescopically rotating the outer C-arm 70 relative to the gantry mount 58 and for rotating the inner C-arm 72 relative to the outer C-arm. Each motor assembly 100 includes a servo motor 102 with encoder feedback, gear box 104 to change the turning ratio, drive pulley 106, idler pulleys 108 and belt 110 threaded between the drive pulley and the idler pulleys. One motor assembly 100 is mounted to the gantry mount to move the outer C-arm 70 along an arc relative to the gantry mount and another motor assembly is mounted to the outer C-arm 70 near the center of the arm to move the inner C-arm 70 along the arc relative to the outer C-arm.

Figure 9B:
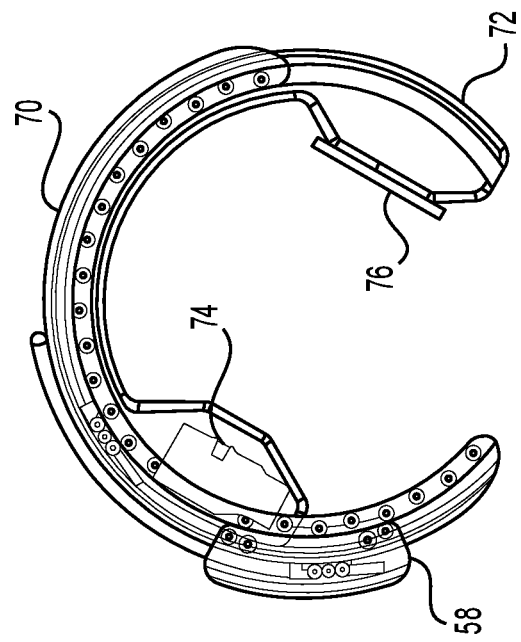
Figure 9A:
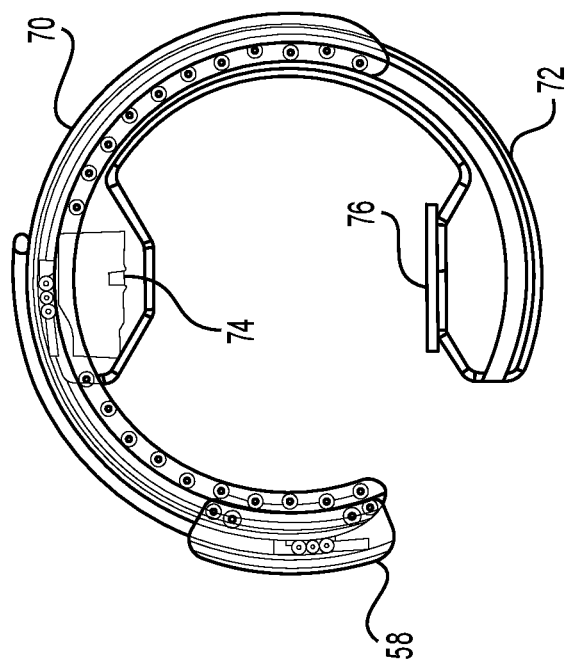
Figure 9D:
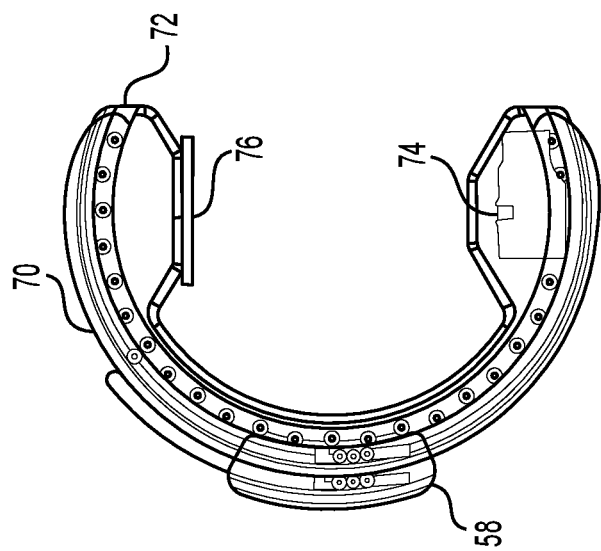
Figure 9C:
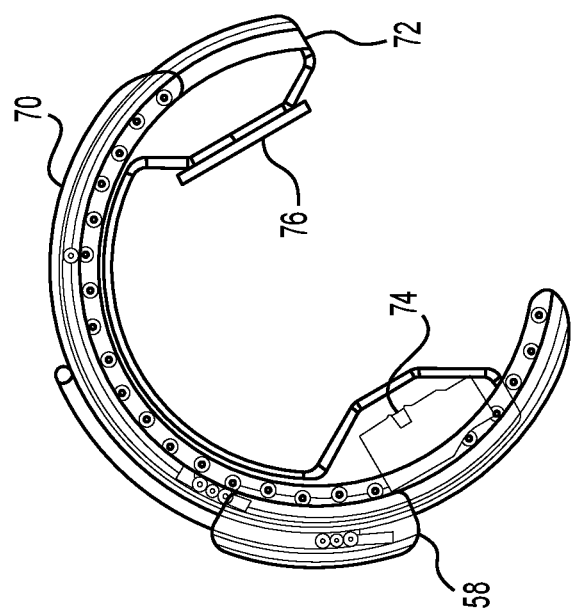
Figure 9F:
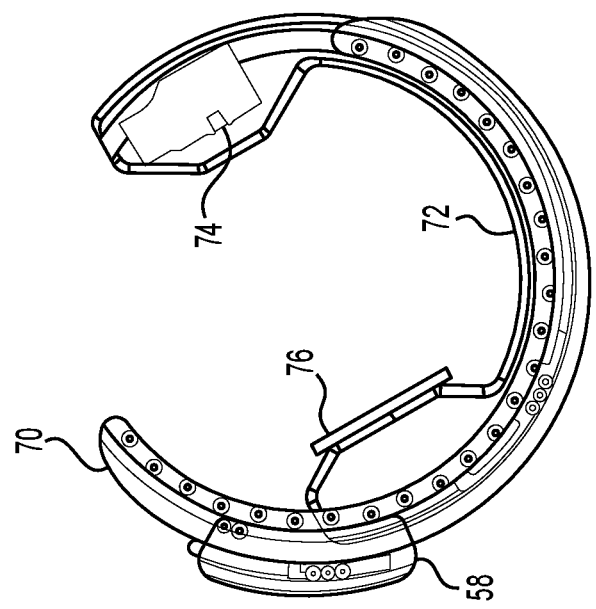
Figure 9E:
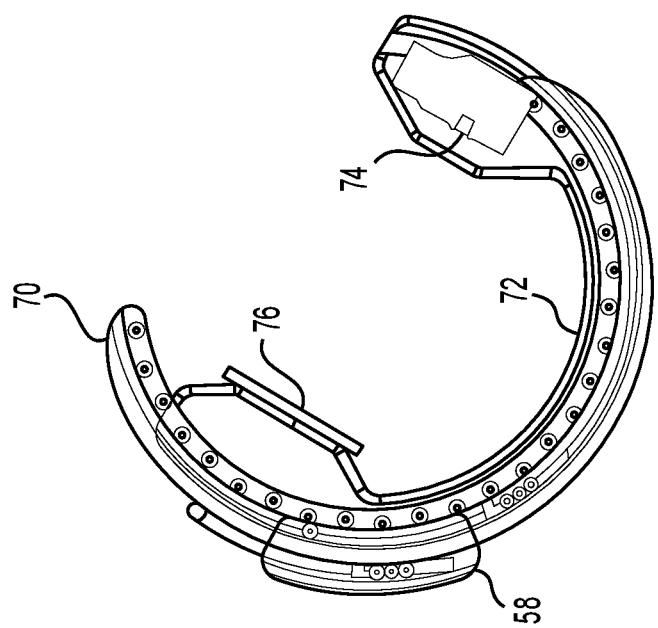

FIGS. 9A-9G illustrate the 360 degree rotation of the gantry 56 in the counter-clockwise direction in 60 degree increments along its arcuate range of motion. FIG. 9A represents a zero degree position of the detector panel 76 and imaging signal transmitter 74. FIG. 9B represents a 60 degree turn/position of the gantry 56. For each 60 degree turn of the gantry 56, the motor assemblies 100, under the control of the motion control module 51, turn the inner C-arm 72 by 30 degrees counter-clock wise along the arc while also turning the outer C-arm 70 by 30 degrees counter-clock wise along the arc for a combined 60 degree turn. FIG. 9G represents a full 360 degree turn of the gantry 56 through its range of motion along the arc. As can be seen, the outer C-arm 70 and inner C-arm 72 have each moved 180 degrees from the original zero degree position of FIG. 9A. Note that the transmitter 74 and detector panel 76 in FIGS. 9D and 9G are reversed from their positions in FIGS. 1 and 9A. This reversal may be advantageous, for example, when it is desirable to have the imaging signal transmitter on one particular side or to have the detector panel on one particular side.

AR System for Use with Medical Imaging Scanner System

Figure 10:
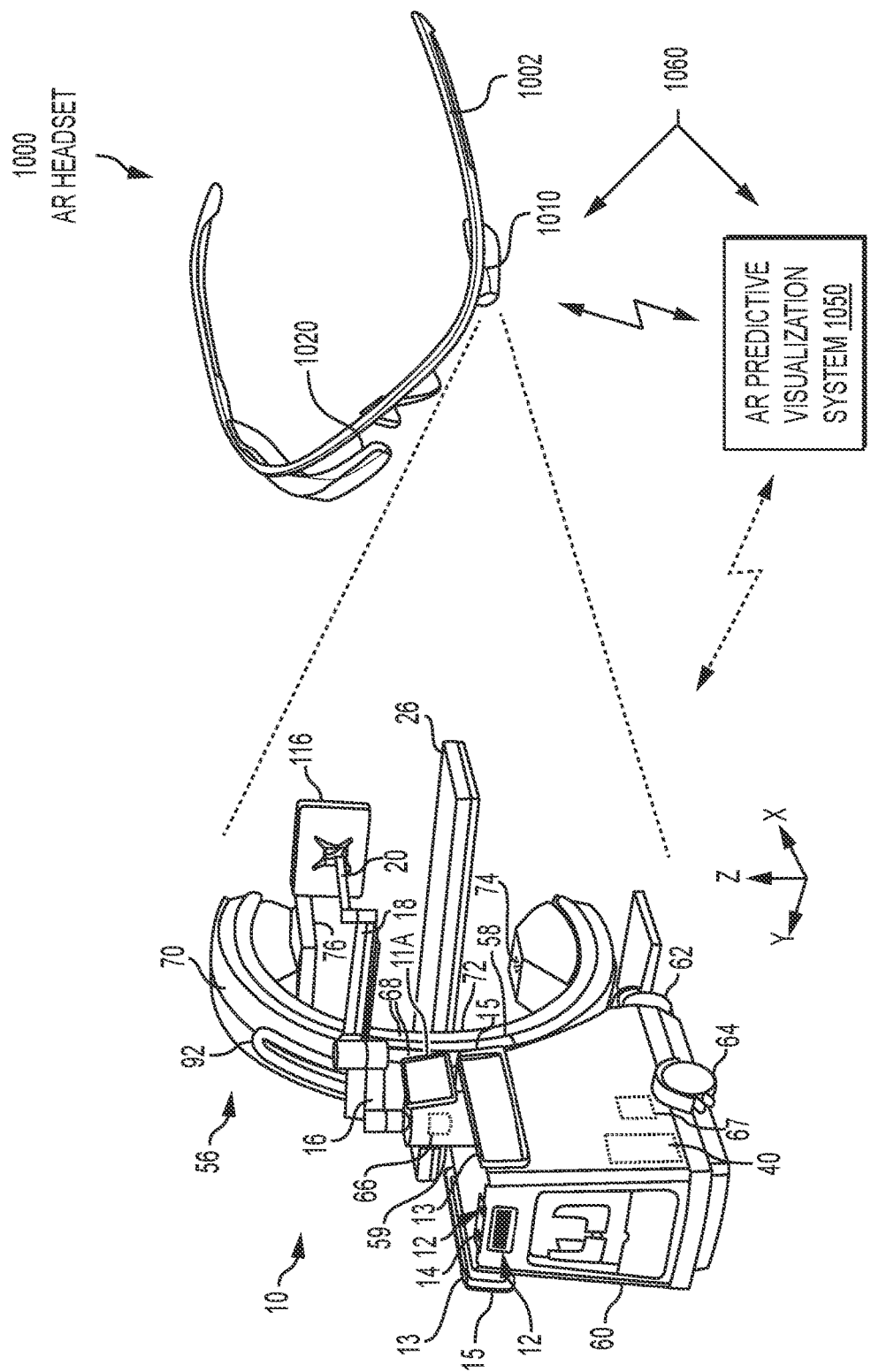
FIG. 10 is a perspective rear view of an AR system with an AR headset that displays graphical objects as overlays on a medical imaging scanner according to some embodiments of the present disclosure.

Embodiments of an AR system 1060 are now described with reference to FIGS. 10 through 16 and which may be used with the medical imaging scanner shown in FIGS. 1 through 9G. FIG. 10 is a perspective rear view of an AR system 1060 with an AR headset 1000. The AR system 1060 enables a user who is wearing the AR headset 1000 to visually observe graphical objects that are displayed as an overlay on the medical imaging scanner 10 to illustrate the range of motion and related operations of the movable scanner components. The graphical objects may provide predictive visualization to the user of how the scanner components can move during an imaging scan.

Although some operational embodiments are discussed in the context of an AR system that displays graphics on a see-through display screen of an AR headset, the disclosed operations may additionally or alternatively be used to display graphics on other types of display screens, such as the displays 11a and 11b connected to the movable station 60 and/or other displays mounted elsewhere in the operating room.

When setting up the imaging scanner 10 for use, the C-arms 70 and 72, to which the imaging signal transmitter 74 and detector panel 76 are mounted, come in from the side of the table 26. Then, during an imaging scan, the C-arms 70 and 72 automatically rotate in a circle around an imaging center, where a patient may reside on a table 26. Predictive visualization can be beneficially used during setup to visualize the range of motion and arcuate paths of the C-arms 70 and 72 if they were to move during an imaging scan. The AR system 1060 enables a user, without operationally starting an imaging scan, to visualize if one or both of the C-arms 70 and 72 is able to clear any obstructions in the path, such as the table 26, a patient, and/or other adjacent objects or equipment.

In a first approach, the AR system 1060 determines the range of motion and the translational and/or rotational movement of the scanner components during a scan, using a defined physical and operational model of relevant characteristics of the components and the supporting C-arm(s), and which may also model their operational environment (e.g., relative motion, speed, and/or acceleration). The AR system 1060 may display on the display screen 1020 a graphical animation of the movable components moving through their arcuate path. A potential disadvantage of this approach is that it relies on a detailed physical and operational model of the imaging system 10, which is limited to use with that particular type of imaging system.

Figure 17:
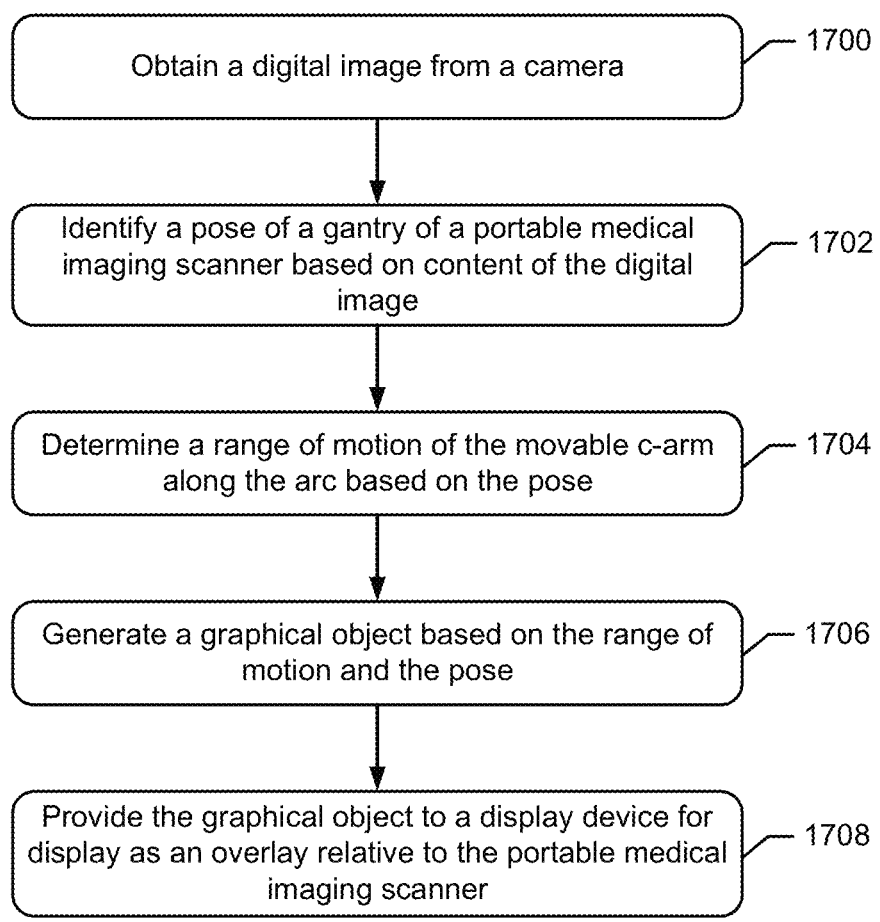
FIG. 17 is a flowchart of operations performed by an AR system in accordance with some embodiments.

In a second approach, the AR system 1060 performs image processing of the digital images from the camera 1010 to identify a feature of the gantry 56, such as detectable features (e.g., edges) of tracks, the imaging signal transmitter 74, the detector panel 76, or the C-arm(s) 70 and/or 72. The identified feature is used to determine a pose (i.e., dimensional location and/or angular orientation) of the movable component of the imaging scanner 10, such as a pose of the imaging signal transmitter 74 and/or the detector panel 76. Alternatively or additionally, the image processing can identify within the digital image from the camera 1010 a location and orientation of a plurality of spaced-apart navigation markers connected to the gantry 56, and identify a pose of at least one of the imaging signal transmitter 74 and the detector panel 76 based on the location and orientation of the plurality of spaced-apart tracking markers. If these tracking markers are spaced in a particular unique pattern, the tracking system can use the spacing pattern to detect and identify the location of the component to which the markers are attached. The second approach is further described below with reference to FIGS. 10 and 17, although various of the described operations may also be used with the first approach. FIG. 17 is a flowchart of operations and methods that may be performed by the AR system 1060.

Referring to FIGS. 10 and 17, the AR headset 1000 includes a display screen 1020, a camera 1010, and a processor 1510 (shown in FIG. 15) which are connected to and supported by a headset frame 1002. The camera 1010 outputs a digital image that may be a single image or a frame of a video stream. In the illustration of FIG. 10 the camera 1010 outputs 1700 a digital image of the medical imaging scanner 10 within the field-of-view of the camera 1010. Content of the digital image is processed to identify 1702 a pose of the gantry 56 of the medical imaging scanner 10. As explained above, the gantry 56 includes a movable C-arm (e.g. first C-arm 70 and second C-arm 72) that supports an imaging signal transmitter 74 and a detector panel 76 that are movable along an arc relative to the station 60. A range of motion of the movable C-arm along the arc is operationally determined 1704 based on the pose. A graphical object is operationally generated 1706 based on the range of motion and the pose, and is provided 1708 to the display screen 1020 for display as an overlay relative to the medical imaging scanner 10.

Figure 16:
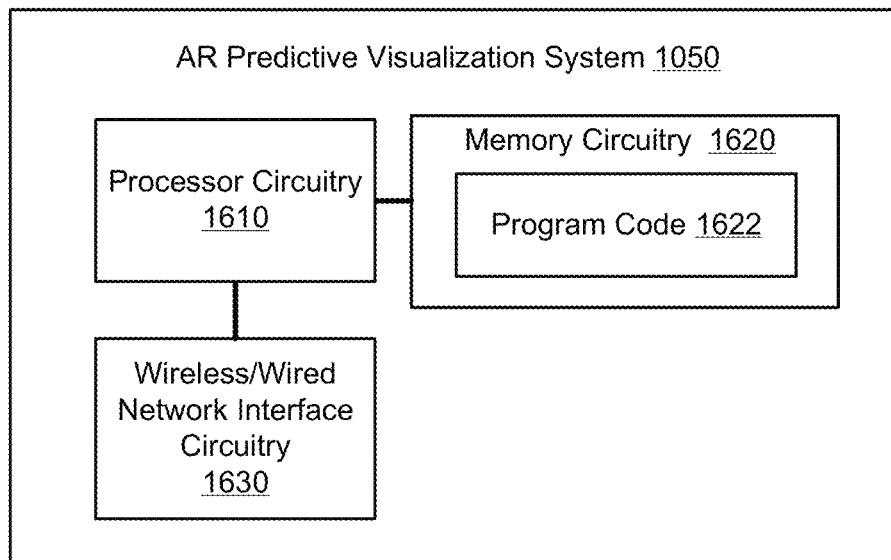
FIG. 16 is a block diagram that illustrates components of an AR predictive visualization computer configured in accordance with some embodiments.

Any one or more of the operations for identifying a pose of the gantry 56, determining the range of motion of the movable C-arm, generating the graphical object, and/or providing the graphical object to the display screen 1020 may be performed by the processor 1510 local to the AR headset 1000 and/or by another processor that is external to the AR headset 1000 and communicatively connected thereto, such as by a processor of an AR predictive visualization computer 1050 (e.g., processor 1610 shown in FIG. 16). The computer 1050 may, for example, be a desktop computer, laptop computer, tablet computer, cellular phone, a network server, or other digital processing device. The AR headset 1000 may be any type of AR headset that is configured to display a graphical object on a display screen that may be seen-through by a user, such as the Google Glass AR headset.

To provide predictive visualization for the imaging scanner 10 and, more particularly, its components that are moved during scanning ("movable components"), e.g., imaging signal transmitter 74 and/or detector panel 76, the AR system 1060 obtains information that defines the range of motion and other related characteristics of the movable components. For example, when the detector panel 76 and the imaging signal transmitter 74 are connected to the first C-arm 70 and the second C-arm 72, respectively, and constrained to travel along an arcuate rail, the AR system generates predictive visualization of motion of the detector panel 76 and the imaging signal transmitter 74 using a transformation matrix. The transformation matrix is used to mathematically transform the positions and angular orientations for one or more components, e.g. the detector panel 76 and the imaging signal transmitter 74, referenced in the coordinate system of the rail to the corresponding positions and angular orientations referenced in the coordinate system of the AR headset 1000. Another transformation matrix can be similarly used to transform the position and/or angular orientation referenced in the coordinate system of the AR headset 1000 to the corresponding positions and/or angular orientations referenced in the coordinate system of the rail and/or another coordinate system defined by the AR system 1060.

The information obtained by the AR system 1060 may define how one or more of the movable components translationally moves and/or rotates while traveling through its range of motion along the rail. The information may further define the speed and/or acceleration with which the one or more movable components travels, which is used to generate the graphical objects that are displayed on the display screen 1020 to provide predictive visualization of such movement.

Figure 11:
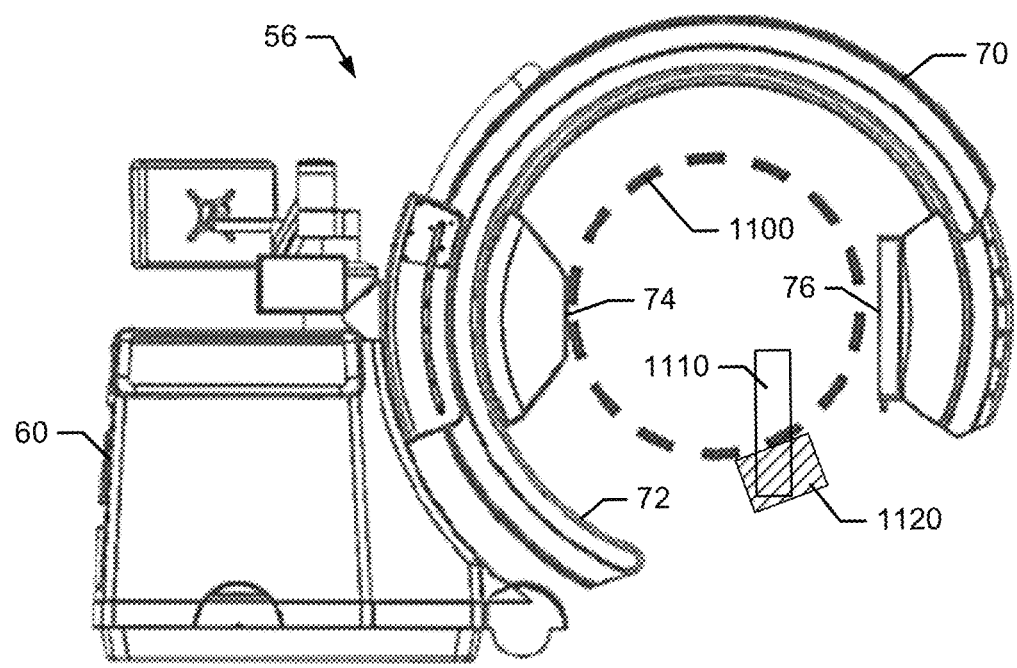
FIG. 11 is a side view of the gantry of the medical imaging scanner as viewed through a display screen of an AR headset that displays a graphical object illustrating an interior region of the movable C-arm that will not be contacted by the C-arm when moved through its range of motion, in accordance with some embodiments.

The AR headset 1000 may display a graphical object that indicates to the user the location of a space, defined by motion of the scanner components, in which the surgical table 26 or other physical object can be positioned while avoiding possible collision with the movable scanner components during an imaging scan. In one embodiment, the AR headset 1000 displays a graphical object that indicates to the user the location of a space, defined by motion of the detector panel 76 and the imaging signal transmitter 74, in which the surgical table 26 or other physical object can be positioned while avoiding possible collision with these components during an imaging scan. FIG. 11 is a side view of the gantry 56 as viewed through the display screen 1020 of the AR headset 1000 that displays a graphical object illustrating an interior region of the movable C-arms 70 and 72 that will not be contacted by the movable components when moved through their range of motion during a scan.

Referring to FIG. 11, the AR system 1060 displays a circular object 1100 as an overlay relative to the gantry 56 and with a pose (i.e., dimensional location and/or angular orientation) that indicates an interior region of the circle that will not be contacted by the imaging signal transmitter 74 and/or the detector panel 76 when they are moved along the arc through their range of motion during an imaging scan. The related operations perform by the AR system 1060 can include identifying the pose of the gantry 56 based on identifying a pose of the imaging signal transmitter 74 and/or the detector panel 76. The range of motion of the imaging signal transmitter 74 and/or the detector panel 76 along the arc is determined based on the pose. An arcuate object, e.g., circular object 1100, is generated and provided to the display screen 1020 for display as an overlay relative to the gantry 56 and with a pose that indicates the range of motion of the imaging signal transmitter 74 and/or the detector panel 76 along the arc. Accordingly, the user can view the imaging scanner 10 through the display screen 1020 to determine where the table 26, a patient, and/or other objects can be placed within the displayed interior region 1100 without risk of collision with movable components of the imaging scanner 10 during a scan. Or when the user looks at the scene through AR glasses with the patient on the table, if any part of the patient or table appears to be outside that circle, which is overlaid on the scene, the user can adjust the position of the imaging system or the position of the table.

The AR system 1060 may perform a collision alert action responsive to determining that a physical object 1110 which is separate from the gantry 56 has a surface that extends from a location within the circular object 1100 displayed on the display screen 1020 to another location 1120 that is outside the circular object 1100.

Figure 12:
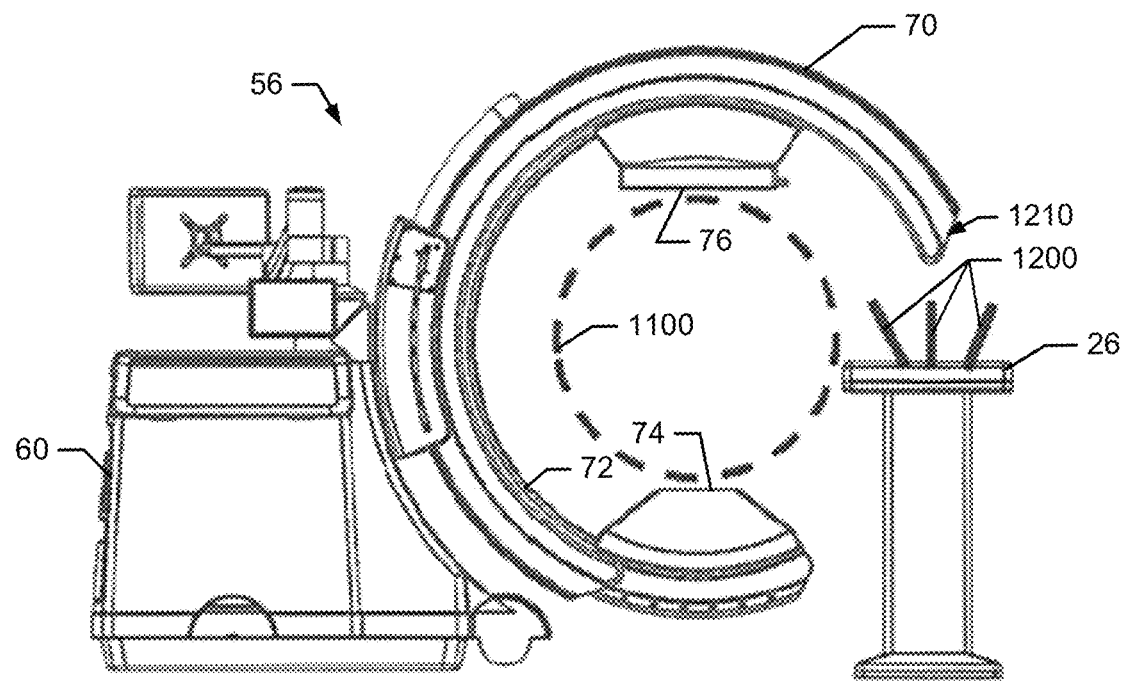
FIG. 12 is a side view of the gantry as viewed through a display screen of an AR headset that displays graphical objects illustrating the collision free interior region of the movable C-arm and indicating that a surgical table has a risk of collision with the C-arm when moved through its range of motion, in accordance with some embodiments.

In one embodiment, the collision alert action performed by the AR system 1060 generates another graphical object that is provided for display on the display screen 1020 as an overlay relative to the physical object and that identifies the physical object as being a collision risk. FIG. 12 is a side view of the gantry 56 as viewed through the display screen 1020 that displays a graphical object indicating that the surgical table 26 has a risk of collision with the movable components when they are moved through their range of motion. In the illustration of FIG. 12, the AR system 1060 has identified through the digital picture from the camera 1010 that the table 26 is located in the pathway of the C-arm(s) 70,72 during an imaging scan and, responsive thereto, has displayed brightly colored or flickering rays 1200 overlaid with a top surface of the table 26 to draw the user's attention to the risk that an end portion 1210 of the C-arm 70 will impact the top surface of the table 26. Other graphical objects may be generated by the AR system 1060 to alert the user as to the risk of collision with an object that is identified through the digital picture from the camera 1010 as being within a pathway of the movable components of the gantry 56.

In another embodiment, the collision alert action performed by the AR system 1060 communicates a command to the medical imaging scanner 10 that disables electronic movement of the gantry 56 for an imaging scan and, more particularly, the movable C-arms 70 and 72, at least in a direction that may collide with the physical object. The AR system 1060 may communicate another command to the medical imaging scanner 10 that re-enables electronic movement of the gantry 56 when another digital picture from the camera 1010 indicates that the physical object is no longer in a pathway of the movable components of the gantry 56.

In another embodiment, the AR system 1060 changes sets a color of the circular object 1100 to indicate whether there is a risk of the movable components colliding with a physical object. For example, the circular object 1100 may be rendered in a green color when no risk of collision is identified and, in contrast, rendered in a red color when a risk of collision is identified.

The AR system 1060 may provide graphical animation through the display screen 1020 that shows the user a predictive visualization of how the moving components of the gantry 56 will move along their pathways during an imaging scan. The operations by the AR system 1060 can include determining a range of motion of an end of the movable C-arm along the arc, e.g., end 1210. The operation of providing the graphical object to the display screen 1020 include displaying a graphical object as an overlay that extends from a present location of the ends of the movable C-arms 70 and 72 to a spaced-apart location along the arc that is within their ranges of motion during a scan. For example, the AR system 1060 may graphically animate rotation of the C-arms 70 and 72 from a fully retracted position to a fully extended position.

While providing a graphical animation of the movable components of the gantry 56, the AR system 1060 may also determine that a physical object, which is separate from the gantry 56, has a surface that is intersected by one of the graphical objects being moved in the animation and, responsive thereto, provide another graphical object for display on the display screen 1020 as an overlay relative to the physical object that identifies the physical object as being a collision risk for one or more of the movable components, such as an end of the movable C-arm, when moved along the arc through its range of motion.

In another embodiment, while providing a graphical animation of the movable components of the gantry 56, the AR system 1060 may also determine that a physical object, which is separate from the gantry 56, has a surface that is intersected by one of the graphical objects being moved in the animation and, responsive thereto, communicating a command to the medical imaging scanner 10 that disables electronic movement of the gantry 56 for an imaging scan (e.g., the movable C-arms 70 and 72) at least in a direction that may collide with the physical object.

Some other embodiments are directed to the AR system 1060 displaying graphical representations of the imaging signal transmitter 74 and the detector panel 76 that are rotated to one or more defined locations. For example, while viewing the imaging scanner 10 through the display screen 1020, the AR system 1060 may display graphical objects that show where the imaging signal transmitter 74 and the detector panel 76 were located along the arc during a previous imaging scan, and/or where they need to be rotated to perform a next imaging scan at a desired offset angle through a patient. Enabling a user to view graphical representations of the imaging signal transmitter 74 and the detector panel 76 from a prior imaging scan can allow the user to optimally position those components for a subsequent lateral scan and/or anteroposterior scan centered on the anatomy of interest.

Figure 13:
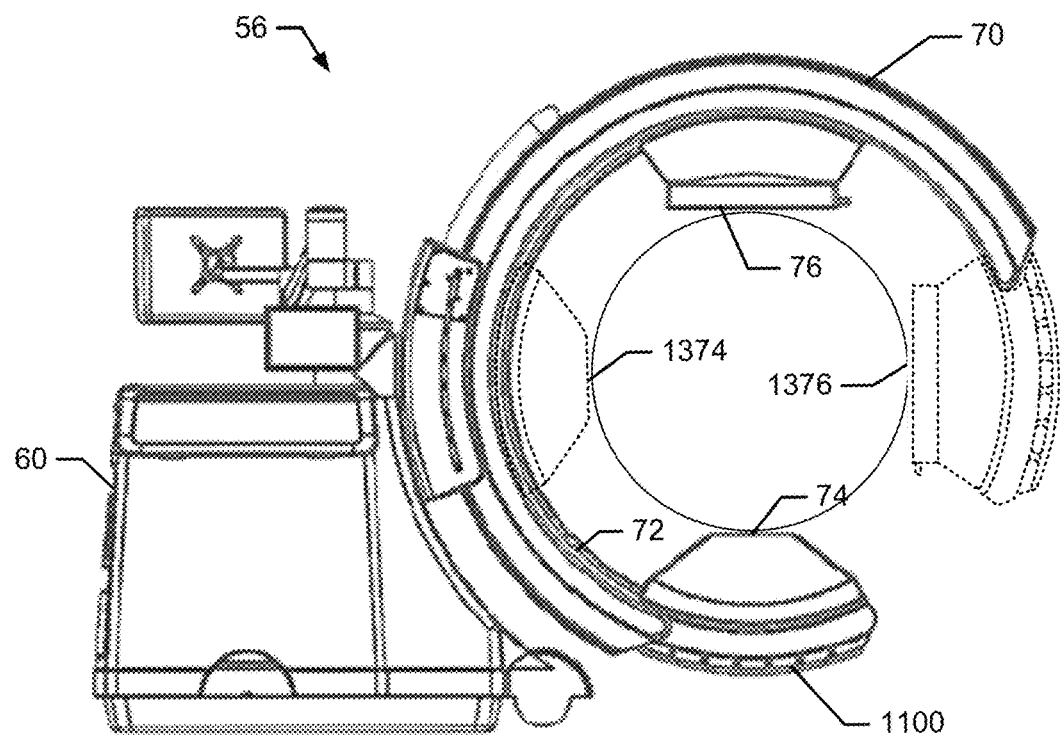
FIG. 13 is a side view of the gantry as viewed through a display screen of an AR headset that displays graphical objects illustrating earlier defined locations and/or future defined locations of an imaging signal transmitter and a detector panel, in accordance with some embodiments.

The related operations performed by the AR system 1060 are explained below with reference to FIG. 13. FIG. 13 is a side view of the gantry 56 as viewed through a display screen 1020 that displays graphical objects which illustrate earlier defined locations and/or future defined locations of the imaging signal transmitter 74 and the detector panel 76. The operations can include identifying a pose (i.e., dimensional location and/or angular orientation) of at least one of the imaging signal transmitter 74 and the detector panel 76. A first graphical object 1374 is generated that represents the imaging signal transmitter 74 and has a first pose that is rotated and offset to a first location along the arc relative to a present location of the imaging signal transmitter 74. Similarly, a second graphical object 1376 is generated that represents the detector panel 76 and has a second pose that is rotated and offset to a second location along the arc relative to a present location of the detector panel 76. The first and second graphical objects 1374 and 1376 are provided to the display screen 1020 for display as an overlay relative to the gantry 56 and with the respective first and second poses.

The operations of generating the graphical object can be repeated for a plurality of locations along the arc, with the generated graphical objects being provided to the display screen 1020 to animate repetitive movement of the imaging signal transmitter 74 and the detector panel 76 through at least part of the range of motion along the arc.

Some other embodiments are directed to the AR system 1060 displaying virtual imaging signal beams that extend between the imaging signal transmitter 74 and the detector panel 76 according to their present locations, defined previous locations, and/or defined future locations, to facilitate the user's positioning of these components relative to a patient to perform a sequence of imaging scans. Enabling a user to view virtual imaging signal beams can allow the user to optimally position the imaging signal transmitter 74 and the detector panel 76 for a lateral scan and/or anteroposterior scan centered on the anatomy of interest. For example, moving from an anterior-posterior scan position to a lateral scan position occurs with the AR headset 1000 displaying a virtual imaging signal beam of the imaging signal transmitter 74 from a prior imaging position, so that the operator may rotate the C-arm to a desired offset angle relative to the earlier scan and centered on the anatomy of interest.

Figure 14:
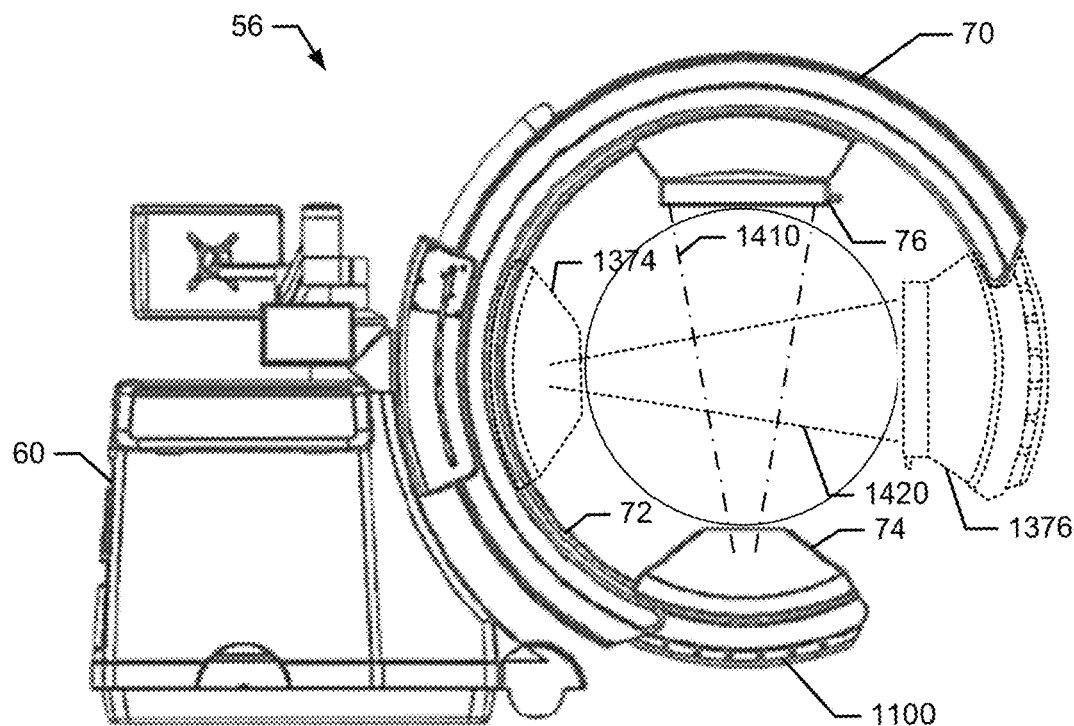
FIG. 14 is a side view of the gantry as viewed through a display screen of an AR headset that displays a virtual imaging signal beam extending between the present locations of the imaging signal transmitter and the detector panel, and displays another virtual imaging signal beam that extends between earlier defined locations of the imaging signal transmitter and the detector panel, in accordance with some embodiments.

Various related operations are described with reference to FIG. 14. FIG. 14 is a side view of the gantry 56 as viewed through the display screen 1020 that displays a virtual imaging signal beam extending between the present locations of the imaging signal transmitter 74 and the detector panel 76, and displays another virtual imaging signal beam that extends between earlier defined locations of the imaging signal transmitter 74 and the detector panel 76.

The operations performed by the AR system 1060 to identify the pose of the gantry 56 can include identifying present locations of the imaging signal transmitter 74 and the detector panel 76. Generation of a graphical object can include generating a second virtual imaging signal beam 1410 that is provided to the display screen 1020 for display as an overlay relative to the gantry 56 and extending from a present location of the imaging signal transmitter 74 to a present location of the detector panel 76. Generation of a graphical object may alternatively or additionally include generating a first virtual imaging signal beam 1420 that is provided to the display screen 1020 for display as an overlay relative to the gantry 56 and extending from an earlier defined location of the imaging signal transmitter 74 to an earlier defined location of the detector panel 76. The earlier defined location locations may correspond to where the imaging signal transmitter 74 and detector panel 76 were previously located during an earlier imaging scan. Accordingly, a user who is looking through the display screen 1020 at the gantry 56 can visually observe the location of the first virtual imaging signaling beam 1420 while rotating the gantry 56 to position the imaging signal transmitter 74 and detector panel 76 to the location where the second virtual imaging signal beam 1410 is visually observed as intersecting the first virtual imaging signal beam 1420 with an angle that is desired, e.g., about 90 degrees, for a next imaging scan.

As explained above, the operations disclosed herein may be used to display graphics on the displays 11a and 11b connected to the movable station 60 and/or on other displays mounted elsewhere in the operating room. The AR system 1060 can include a camera that is connected to a tripod or other structure and positioned to view the medical imaging scanner 10 and to output a video stream of digital image frames showing the medical imaging scanner 10. The predictive visualization system 1050 is connected to receive the video stream from the camera, and to add graphical objects positionally overlaid on the digital image frames relative to the medical imaging scanner 10 to generate a composite video stream that is provided to the display(s), e.g., displays 11a and 11b and/or other displays. The graphical objects added to form the composite video stream can illustrate the path of the movable components of the scanner 10 and related collision risks, past and/or target future locations of the movable components, and/or related virtual imaging signal beams in accordance with any one or more of the embodiments disclosed herein.

Accordingly, various embodiments disclosed herein provide an improved user interface for operating a medical imaging system. The AR system 1060 provides an intuitive user interface that can improve safety of operation of the medical imaging system and improve quality of the images that are generated from a sequence of image scans through a patient at different angles.

Components of AR Headset and AR Predictive Visualization Computer

Figure 15:
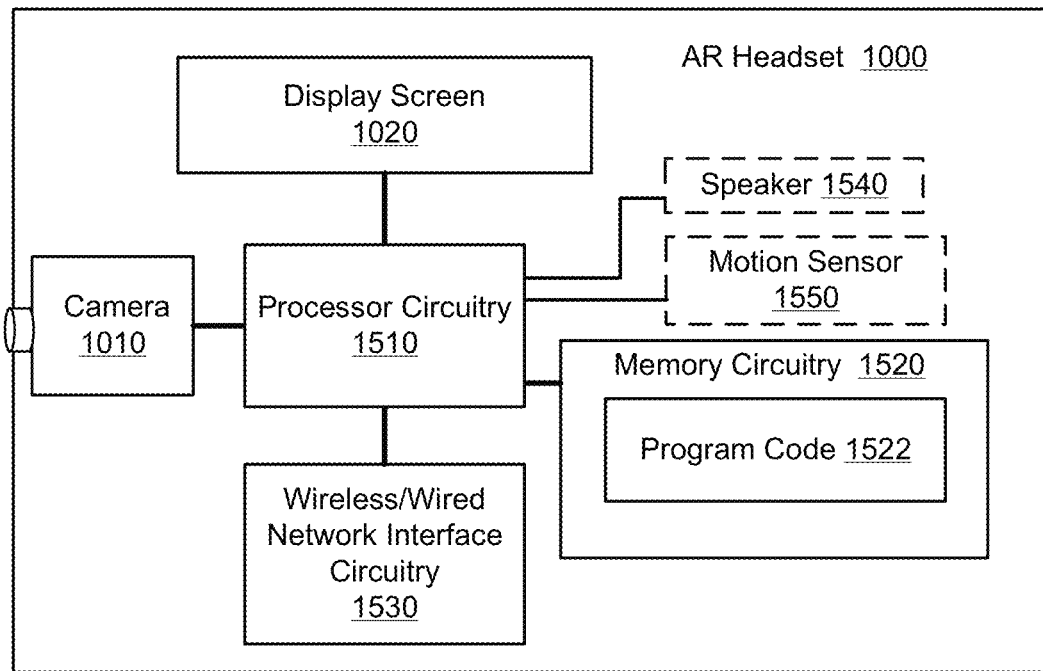
FIG. 15 is a block diagram that illustrates components of an AR headset configured in accordance with some embodiments.

FIG. 15 is a block diagram that illustrates components of an AR headset 1000 that is configured in accordance with some embodiments. The AR headset 1000 can include a camera 1010, a display screen 1020, at least one processor circuit 1510 (processor), and at least one memory 1520 (memory). The display screen 1020 may be a see-through screen that displays graphical images for viewing by a user while allowing transmission of incident ambient light from physical objects to pass therethrough to the user for viewing. The processor is connected to the camera 1010, the display screen 1020, and the memory 1520. The memory 1520 stores program code 1522 that is executed by the processor 1510 to perform operations. The processor 1510 may include one or more data processing circuits, such as a general purpose and/or special purpose processor (e.g., microprocessor and/or digital signal processor), which may be collocated or distributed across one or more data networks. The processor 1510 is configured to execute computer program instructions among program code 1522 in the memory 1520, described below as a computer readable medium, to perform some or all of the operations and methods for one or more of the embodiments disclosed herein for a AR headset 1000. They are headset 1000 may include a wireless and/or wired network interface circuit 1530 that is configured to communicate with another electronic device, such as the AR predictive visualization computer 1050 and/or the imaging scanner 10, through a wired (e.g., ethernet, USB, etc.) and/or wireless (e.g., Wi-Fi, Bluetooth, cellular, etc.) network.

FIG. 16 is a block diagram that illustrates components of an AR predictive visualization computer 1050 that is configured in accordance with some embodiments. The computer 1050 can include a wireless and/or wired network interface circuit 1630, at least one processor circuit 1610 (processor), and at least one memory 1620 (memory). The network interface circuit 1630 is configured to communicate with another electronic device, such as the AR headset 1000 and/or the imaging scanner 10, through a wired (e.g., ethernet, USB, etc.) and/or wireless (e.g., Wi-Fi, Bluetooth, cellular, etc.) network. The processor 1610 is connected to network interface 1630 in the memory 1620. The memory 1620 stores program code 1622 that is executed by the processor 1610 to perform operations. The processor 1610 may include one or more data processing circuits, such as a general purpose and/or special purpose processor (e.g., microprocessor and/or digital signal processor), which may be collocated or distributed across one or more data networks. The processor 1610 is configured to execute computer program instructions among program code 1622 in the memory 1620, described below as a computer readable medium, to perform some or all of the operations and methods for one or more of the embodiments disclosed herein for an AR predictive visualization computer.

When the AR predictive visualization system 1050 is used with a non-head mounted display and camera, the display and camera may be connected to the processor circuitry 1610 through the network interface circuitry 1630 which can include parallel video input and output circuits, such as HDMI, DisplayPort, Digital Visual Interface, and/or other video interface circuitry.

Further Definitions and Embodiments

In the above description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

For purposes of this application, the terms "code", "software", "program", "application", "software code", "software module", "module" and "software program" are used interchangeably to mean software instructions that are executable by a processor.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method of using a medical imaging scanner comprising:
    under the control of a processor,
        obtaining a digital image of the medical imaging scanner from a camera;
        identifying by the processor a pose of a gantry of the medical imaging scanner based on the obtained digital image, the gantry including a movable C-arm supporting an imaging signal transmitter and a detector panel that are movable along an arc relative to a station;
        predictively determining a range of motion of the movable C-arm along the arc based on the pose without moving the movable C-arm;
        generating a graphical object based on the predictive determination of the range of motion and the pose, wherein the graphical object indicates a clearance region that will not be contacted by the imaging signal transmitter and the detector panel during imaging; and
        displaying the generated graphical object on an augmented reality (AR) display device as an overlay to the medical imaging scanner,
    wherein the step of displaying the graphical object on the AR display device includes providing an arcuate object for display as an overlay relative to the gantry and with a pose that indicates the range of motion of the at least one of the imaging signal transmitter and the detector panel along the arc, and
    wherein the step of providing the arcuate object for display includes providing a circular object for display as an overlay relative to the gantry and with a pose that indicates an interior region of the movable C-arm that will not be contacted by the at least one of the imaging signal transmitter and the detector panel when moved along the arc through the range of motion.

2. The method of claim 1, wherein:
the step of identifying the pose of the gantry includes identifying a pose of at least one of the imaging signal transmitter and the detector panel; and
the step of determining the range of motion of the movable C-arm along the arc includes determining a range of motion of the at least one of the imaging signal transmitter and the detector panel along the arc.

3. The method of claim 1, further comprising:
determining that a physical object which is separate from the gantry has a surface that extends from a location within the circular object displayed on the AR display device to another location that is outside the circular object; and
performing a collision alert action responsive to the determination.

4. The method of claim 3, wherein:
performing the collision alert action comprises providing another graphical object for display as an overlay relative to the physical object and that identifies the physical object as being a collision risk for the at least one of the imaging signal transmitter and the detector panel when moved along the arc through the range of motion.

5. The method of claim 3, wherein:
performing the collision alert action comprises communicating a command to the medical imaging scanner that disables electronic movement of the movable C-arm at least in a direction that may collide with the physical object.

6. The method of claim 1, wherein:
the step of determining the range of motion of the movable C-arm along the arc comprises determining a range of motion of an end of the movable C-arm along the arc; and
the step of providing the graphical object to the AR display device comprises providing the graphical object to the AR display device as an overlay that extends from a present location of the end of the movable C-arm to a spaced-apart location along the arc that is within the range of motion of the end of the movable C-arm.

7. The method of claim 6, further comprising:
determining that a physical object that is separate from the gantry has a surface that is intersected by the graphical object; and
providing another graphical object for display as an overlay relative to the physical object and that identifies the physical object as being a collision risk for the end of the movable C-arm when moved along the arc through the range of motion.

8. The method of claim 6, further comprising:
determining that a physical object that is separate from the gantry has a surface that is intersected by the graphical object; and
communicating a command to the medical imaging scanner that temporarily disables electronic movement of the movable C-arm at least in a direction that may collide with the physical object, responsive to the determination that the surface of the physical object is intersected by the graphical object.

9. The method of claim 1, wherein:
the step of identifying the pose of the gantry comprises identifying a pose of at least one of the imaging signal transmitter and the detector panel;
the step of generating the graphical object based on the range of motion and the pose comprises generating a first graphical object that represents the imaging signal transmitter and has a first pose that is rotated and offset to a first location along the arc relative to a present location of the imaging signal transmitter, generating a second graphical object that represents the detector panel and has a second pose that is rotated and offset to a second location along the arc relative to a present location of the detector panel; and
the step of providing the graphical object to the AR display device comprises providing the first and second graphical objects for display as an overlay relative to the gantry and with the respective first and second poses.

10. The method of claim 9, further comprising:
repeating the steps of generating the graphical object for a plurality of locations along the arc and providing the graphical object to the AR display device to animate repetitive movement of the imaging signal transmitter and the detector panel through at least part of the range of motion along the arc.

11. The method of claim 1, wherein:
the step of identifying the pose of the gantry comprises identifying present locations of the imaging signal transmitter and the detector panel;
the step of generating the graphical object comprises generating a first virtual imaging signal beam and a second virtual imaging signal beam; and
the step of displaying the graphical object on the AR display device comprises:
providing the first virtual imaging signal beam for display as an overlay relative to the gantry and extending from an earlier defined location of the imaging signal transmitter to an earlier defined location of the detector panel; and
providing the second virtual imaging signal beam for display as another overlay relative to the gantry and extending from a present location of the imaging signal transmitter to a present location of the detector panel.

12. The method of claim 1, further comprising:
generating a graphical image indicative of an imaging beam path between the imaging signal transmitter and the detector panel; and
displaying the generated graphical image on the AR display as an overlay to the medical imaging scanner.

13. The method of claim 1, wherein:
generating a graphical image representing the locations of the detector panel and the imaging signal transmitter for a next image to be taken;
displaying the generated graphical image on the AR display as an overlay to the medical imaging scanner.

14. The method of claim 1, wherein:
the operation of identifying the pose of the gantry comprises identifying within the digital image a location and orientation of a plurality of spaced-apart navigation markers connected to the gantry, and identifying a pose of at least one of the imaging signal transmitter and the detector panel based on the location and orientation of the plurality of spaced-apart navigation markers.

15. A method of using a medical imaging scanner with an augmented reality (AR) display device, the method comprising:
under the control of a processor of a computer system:
obtaining a digital image of the medical imaging scanner from the camera;
identifying a pose of a gantry of the medical imaging scanner based on content of the digital image, the gantry including a movable C-arm supporting an imaging signal transmitter and a detector panel that are movable along an arc relative to a station;
determining a range of motion of the movable C-arm along the arc based on the pose;
generating a graphical object indicative of a clearance region based on the range of motion and the pose; and
providing the graphical object to the AR display device for display as an overlay relative to the medical imaging scanner,
wherein the step of providing the graphical object to the AR display device includes providing an arcuate object for display as an overlay relative to the gantry and with a pose that indicates the range of motion of the at least one of the imaging signal transmitter and the detector panel along the arc, and
wherein the step of providing the arcuate object for display includes providing a circular object for display as an overlay relative to the gantry and with a pose that indicates an interior region of the movable C-arm that will not be contacted by the at least one of the imaging signal transmitter and the detector panel when moved along the arc through the range of motion.

16. The method of claim 15, wherein:
the computer system includes a headset frame,
the AR display device includes a see-through display screen that displays graphical images while allowing transmission of incident ambient light therethrough,
the camera, the AR display device, and the processor are each supported by connection to the headset frame, and
the processor determines the dimensional location and angular orientation of the imaging signal transmitter and the detector panel from navigation markers attached to the imaging scanner.

17. The method of claim 15, wherein:
the AR display device is part of an AR headset; and
the AR headset includes a network interface, the camera, and a first processor which is configured to perform the operation of obtaining the digital image from the camera and an operation of communicating the digital image through the network interface toward an AR predictive visualization computer, wherein the AR display device includes a see-through display screen that displays graphical images while allowing transmission of incident ambient light therethrough, and
wherein the AR predictive visualization computer comprises a network interface configured to communicate with the network interface of the AR headset, a second processor which is configured to perform the operations of identifying the pose of the gantry, determining the range of motion of the movable C-arm, generating the graphical object, and providing the graphical object through the network interface toward the AR headset for display on the display screen.

18. The method of claim 15, wherein:

the step of identifying the pose of the gantry comprises identifying a pose of at least one of the imaging signal transmitter and the detector panel;

the step of generating the graphical object based on the range of motion and the pose comprises generating a first graphical object that represents the imaging signal transmitter and has a first pose that is rotated and offset to a first location along the arc relative to a present location of the imaging signal transmitter, generating a second graphical object that represents the detector panel and has a second pose that is rotated and offset to a second location along the arc relative to a present location of the detector panel; and the step of providing the graphical object to the display device comprises providing the first and second graphical objects for display as an overlay relative to the gantry and with the respective first and second poses.

19. The method of claim 15, wherein:

the step of identifying the pose of the gantry comprises identifying present locations of the imaging signal transmitter and the detector panel;

the step of generating the graphical object, comprises generating a first virtual imaging signal beam and a second virtual imaging signal beam; and the step of providing the graphical object to the display device comprises:

providing the first virtual imaging signal beam for display as an overlay relative to the gantry and extending from an earlier defined location of the imaging signal transmitter to an earlier defined location of the detector panel; and providing the second virtual imaging signal beam for display as another overlay relative to the gantry and extending from a present location of the imaging signal transmitter to a present location of the detector panel.

* * * * *